US009789156B2

(12) United States Patent
Kufe et al.

(10) Patent No.: US 9,789,156 B2
(45) Date of Patent: Oct. 17, 2017

(54) COMBINATION ANTI-HUMAN EPIDERMAL GROWTH FACTOR RECEPTOR 2 (ANTI-HER2) CANCER THERAPY USING MUCIN 1 (MUC1) PEPTIDES AND HEMOTHERAPEUTICS

(71) Applicants: DANA-FARBER CANCER INSTITUTE, INC., Boston, MA (US); GENUS ONCOLOGY, LLC, Chicago, IL (US)

(72) Inventors: Donald W. Kufe, Wellesley, MA (US); Surender Kharbanda, Natick, MA (US)

(73) Assignees: Dana-Farber Cancer Institute, Inc., Boston, MA (US); Genus Oncology, LLC, Chicago, IL (US)

( * ) Notice: Subject to any disclaimer, the term of this patent is extended or adjusted under 35 U.S.C. 154(b) by 0 days.

(21) Appl. No.: 14/774,155

(22) PCT Filed: Mar. 10, 2014

(86) PCT No.: PCT/US2014/022269
§ 371 (c)(1),
(2) Date: Sep. 10, 2015

(87) PCT Pub. No.: WO2014/164394
PCT Pub. Date: Oct. 9, 2014

(65) Prior Publication Data
US 2016/0074468 A1    Mar. 17, 2016

Related U.S. Application Data

(60) Provisional application No. 61/776,539, filed on Mar. 11, 2013.

(51) Int. Cl.
*A61K 38/08* (2006.01)
*A61K 38/10* (2006.01)
*A61K 38/17* (2006.01)
*A61K 31/517* (2006.01)
*A61K 39/395* (2006.01)

(52) U.S. Cl.
CPC ............ *A61K 38/10* (2013.01); *A61K 31/517* (2013.01); *A61K 38/08* (2013.01); *A61K 38/1709* (2013.01); *A61K 39/39558* (2013.01)

(58) Field of Classification Search
CPC ...... A61K 31/517; A61K 38/08; A61K 38/10; A61K 38/1709; A61K 39/39558; A61K 39/395
USPC .......... 424/133.1; 514/19.3, 19.4, 19.5, 19.8, 514/21.5, 21.6, 21.7, 21.8, 21.9
See application file for complete search history.

(56) References Cited

U.S. PATENT DOCUMENTS

2009/0148535 A1*  6/2009  Bamdad ............... A61K 9/5115
                                                          424/499
2010/0125055 A1*  5/2010  Kufe ................... A61K 38/1735
                                                          514/1.1

FOREIGN PATENT DOCUMENTS

WO    WO 2010/045586    4/2010

OTHER PUBLICATIONS

Herceptin from Breastcancer.org, p. 1. Accessed Dec. 5, 2016.*
Baldus et al., "MUC1 and nuclear beta-catenin are coexpressed at the invasion front of colorectal carcinomas and are both correlated with tumor prognosis," *Cin. Cancer Res.*, 10(8):2790-2796, 2004.
Berns et al., "A functional genetic approach identifies the PI3K pathway as a major determinant of trastuzumab resistance in breast cancer," *Cancer Cell*, 12:395-402, 2007.
Fessler et al., "MUC1 is a determinant of trastuzumab (Herceptin) resistance in breast cancer cells," *Breast Cancer Research and Treatment*, 118(1):113-124, 2009.
Huang et al., "Heterotrimerization of the growth factor receptors erbB2, erbB3, and insulin-like growth factor-i receptor in breast cancer cells resistant to Herceptin," *Cancer Res.*, 70:1204-14, 2010.
Huang et al., "MUC1 cytoplasmic domain coactivates Wnt target gene transcription and confers transformation," *Cancer Biol. Ther.*, 2:702-706, 2003.
Konecny et al., "Activity of the dual kinase inhibitor lapatinib (GW572016) against HER-2-overexpressing and trastuzumab-treated breast cancer cells," *Cancer Res.*, 66:1630-1639, 2006.
Kufe, "MUC1-C oncoprotein as a target in breast cancer: activation of signaling pathways and therapeutic approaches," *Oncogene*, 32:1073-81, 2013.
Kufe, "Mucins in cancer: function, prognosis and therapy," *Nature Reviews Cancer*, 9:874-85, 2009.
Lee-Hoeflich et al., "PPM1H is a p27 phosphatase implicated in trastuzumab resistance," *Cancer Discov.*, 1:326-37, 2011.
Li et al., "DF3/MUC1 signaling in multiple myeloma cells is regulated by interleukin-7," *Cancer Biol. Ther.*, 2:187-193, 2003.
Li et al., "Heregulin targets gamma-catenin to the nucleolus by a mechanism dependent on the DF3/MUC1 oncoprotein," *Mol. Cancer Res.*, 1:765-775, 2003.
Li et al., "Human DF3/MUC1 carcinoma-associated protein functions as an oncogene," *Oncogene*, 22:6107-6110, 2003.
Li et al., "Interaction of glycogen synthase kinase 3beta with the DF3/MUC1 carcinoma-associated antigen and beta-catenin," *Mol. Cell Biol.*, 18:7216-7224, 1998.
Li et al., "The c-Src tyrosine kinase regulates signaling of the human DF3/MUC1 carcinoma-associated antigen with GSK3 beta and beta-catenin," *J. Biol. Chem.*, 276:6061-6064, 2001.
Li et al., "The epidermal growth factor receptor regulates interaction of the human DF3/MUC1 carcinoma antigen with c-Src and beta-catenin," *J. Biol. Chem.*, 276:35239-35242, 2001.
Mittendorf et al., "A novel interaction between HER2/neu and cyclin E in breast cancer," *Oncogene*, 29:3896-3907, 2010.

(Continued)

*Primary Examiner* — Julie Ha
(74) *Attorney, Agent, or Firm* — Parker Highlander PLLC

(57) ABSTRACT

The treatment of human epidermal growth factor receptor 2-positive (HER2+) cancers using a combination of anti-mucin 1 (anti-MUC1) therapy and anti-human epidermal growth factor receptor 2 (anti-HER2) therapy is described, such as the treatment of trastuzamab-resistant cancers, both primary and acquired, using the same combination of agents.

41 Claims, 10 Drawing Sheets

(56) References Cited

OTHER PUBLICATIONS

Mittendorf et al., "Loss of HER2 amplification following trastuzumab-based neoadjuvant systemic therapy and survival outcomes," *Clin. Cancer Res.*, 15:7381-8, 2009.

Nagata et al., "PTEN activation contributes to tumor inhibition by trastuzumab, and loss of PTEN predicts trastuzumab resistance in patients," *Cancer Cell*, 6:117-27, 2004.

Nahta et al, "Insulin-like growth factor-I receptor/human epidermal growth factor receptor 2 heterodimerization contributes to trastuzumab resistance of breast cancer cells," *Cancer Res.*, 65:11118-28, 2005.

Nahta et al., "Lapatinib induces apoptosis in trastuzumab-resistant breast cancer cells: effects on insulin-like growth factor I signaling," *Mol. Cancer Ther.*, 6:667-674, 2007.

Nahta et al., "P27(kip1) down-regulation is associated with trastuzumab resistance in breast cancer cells," *Cancer Res.*, 64:3981-6, 2004.

PCT International Search Report and Written Opinion issued in International Patent Application No. PCT/US2014/022269, dated Jul. 17, 2014.

Raina et al., "Dependence on the MUC1-C oncoprotein in non-small cell lung cancer cells," *Mol. Cancer Therapeutics*, 10:806-16, 2011.

Raina et al., "Targeting the MUC1-C oncoprotein downregulates HER2 activation and abrogates trastuzumab resistance in breast cancer cells," *Oncogene*, 33(26):3422-3431, 2014.

Raina et al., "The MUC1 oncoprotein activates the anti-apoptotic phosphoinositide 3-kinase/Akt and Bcl-xL pathways in rat 3Y1 fibroblasts," *J. Biol. Chem.*, 279:20607-20612, 2004.

Ren et al., "Protein kinase C delta regulates function of the DF3/MUC1 carcinoma antigen in beta-catenin signaling," *J. Biol. Chem.*, 277:17616-17622, 2002.

Scaltriti et al., "Lapatinib, a HER2 tyrosine kinase inhibitor, induces stabilization and accumulation of HER2 and potentiates trastuzumab-dependent cell cytotoxicity," *Oncogene*, 28:803-14, 2009.

Scaltriti et al., "Cyclin E amplification/overexpression is a mechanism of trastuzumab resistance in HER2+ breast cancer patients," *Proc. Natl. Acad. Sci. USA*, 108:3761-6, 2011.

Scaltriti et al., "Expression of p95HER2, a truncated form of the HER2 receptor, and response to anti-HER2 therapies in breast cancer," *J. Natl. Cancer Inst.*, 99:628-38, 2007.

Schroeder et al., "MUC1 overexpression results in mammary gland tumorigenesis and prolonged alveolar differentiation," *Oncogene*, 23:5739-5747, 2004.

Schroeder et al., "Transgenic MUC1 interacts with epidermal growth factor receptor and correlates with mitogen-activated protein kinase activation in the mouse mammary gland," *J. Biol. Chem.*, 276(16):13057-13064, 2001.

Shattuck et al., "Met receptor contributes to trastuzumab resistance of Her2-overexpressing breast cancer cells," *Cancer Res.*, 68:1471-7, 2008.

Wei et al., "Human MUC1 oncoprotein regulates p53-responsive gene transcription in the genotoxic stress response," *Cancer Cell*, 7:167-178, 2005.

Wen et al., "Nuclear association of the cytoplasmic tail of MUC1 and beta-catenin," *J. Biol. Chem.*, 278:38029-38039, 2003.

Wood et al, "A unique structure for epidermal growth factor receptor bound to GW572016 (Lapatinib): relationships among protein conformation, inhibitor off-rate, and receptor activity in tumor cells," *Cancer Res.*, 64:6652-6659, 2004.

Yamamoto et al., "Interaction of the DF3/MUC1 breast carcinoma-associated antigen and beta-catenin in cell adhesion," *J. Biol. Chem.*, 272:12492-12494, 1997.

Zhang et al., "Combating trastuzumab resistance by targeting SRC, a common node downstream of multiple resistance pathways," *Nat. Med.*, 17:461-9, 2011.

\* cited by examiner

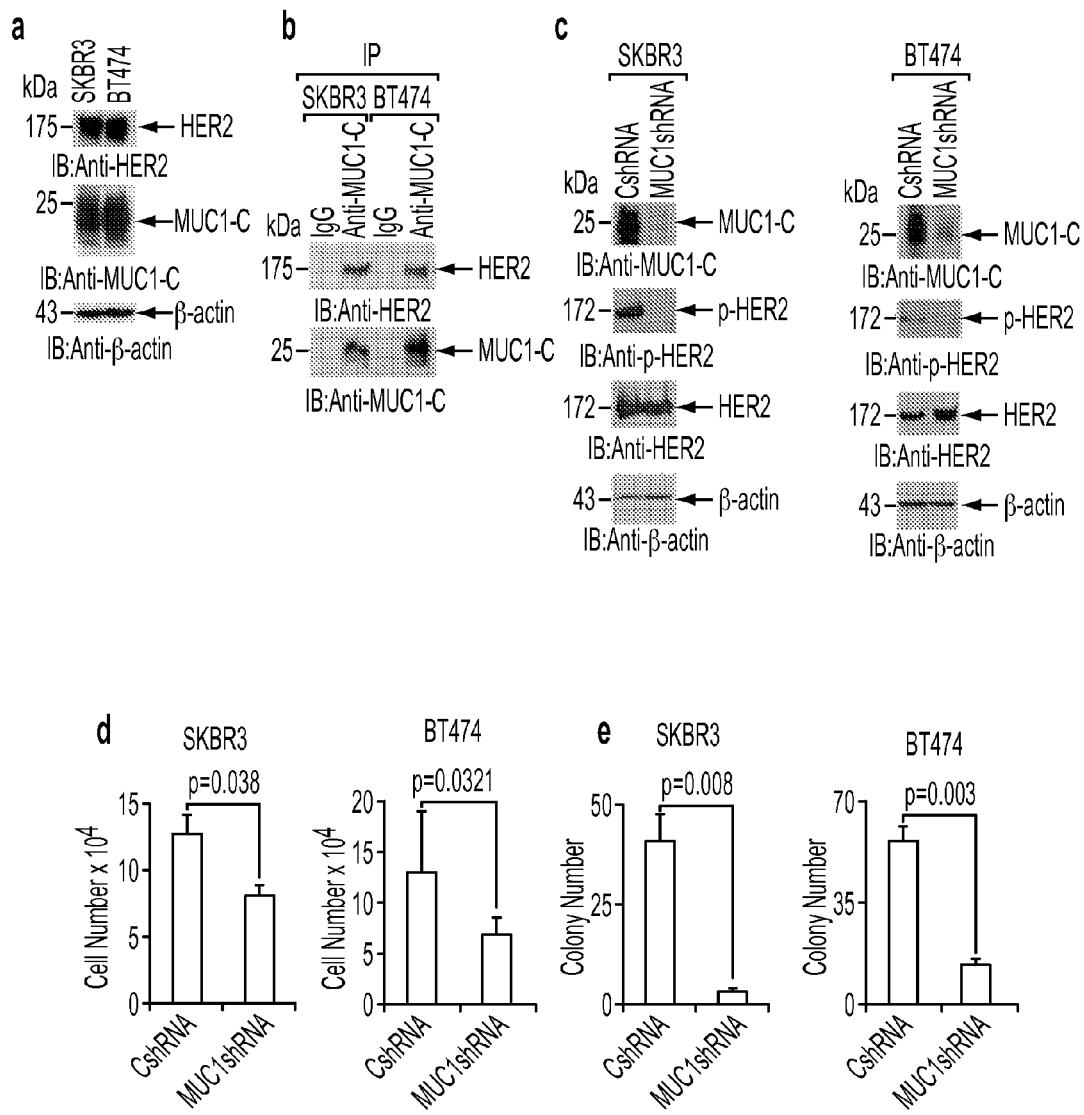
FIGS. 1A-E

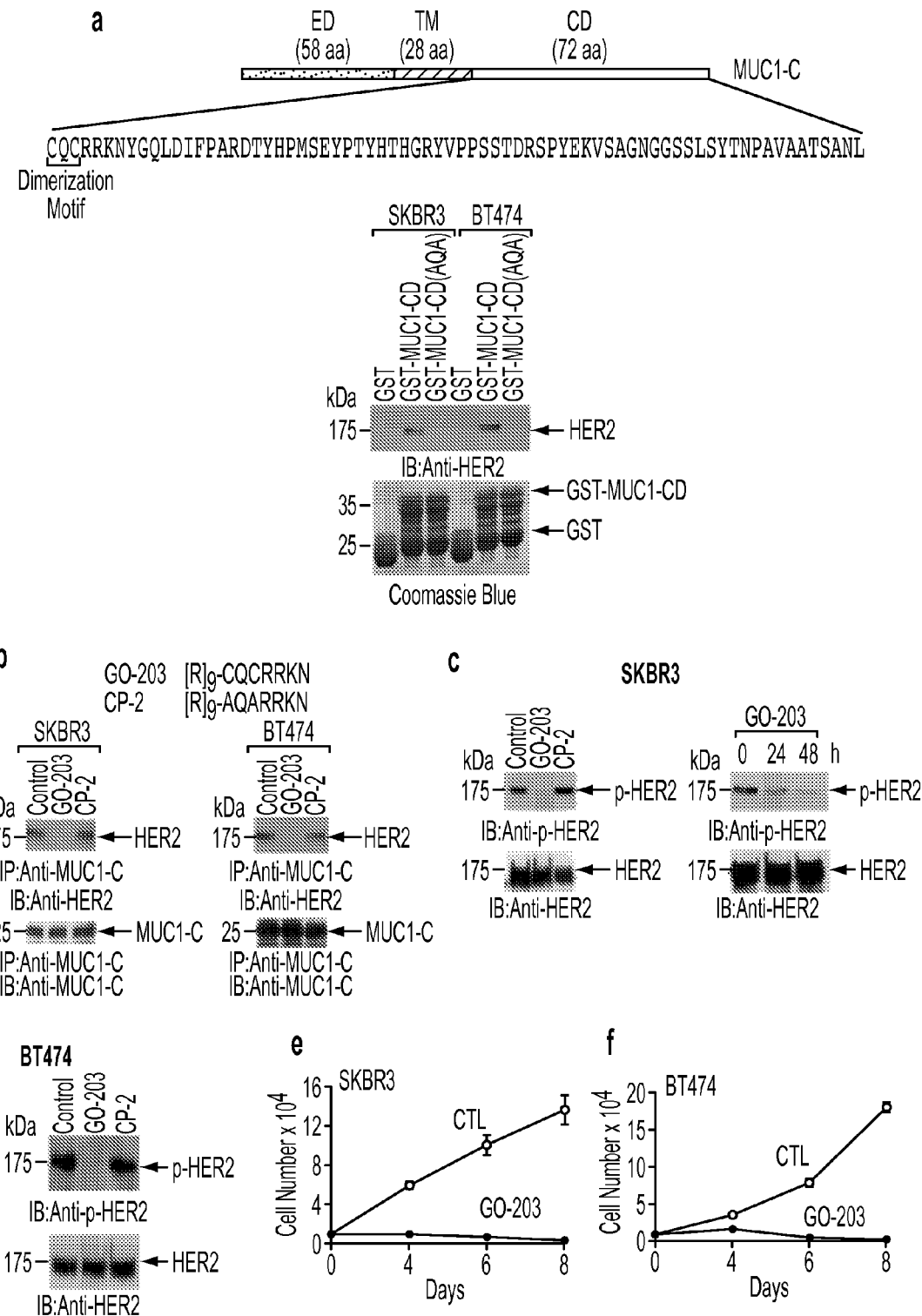
FIGS. 2A-F

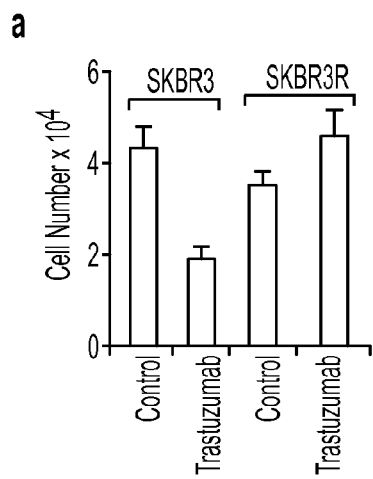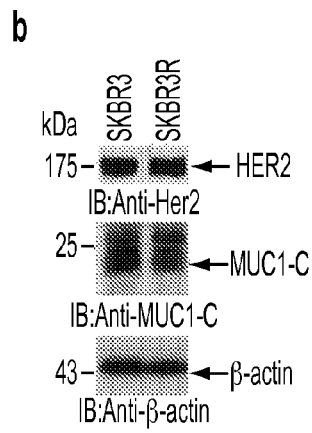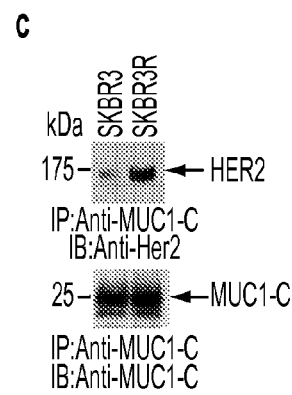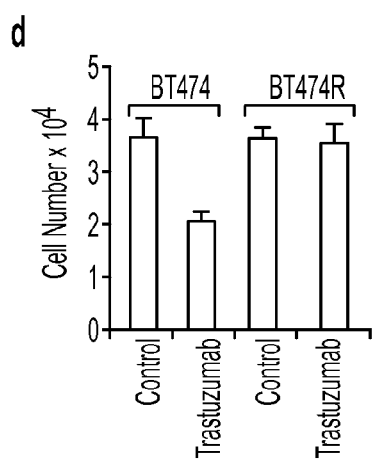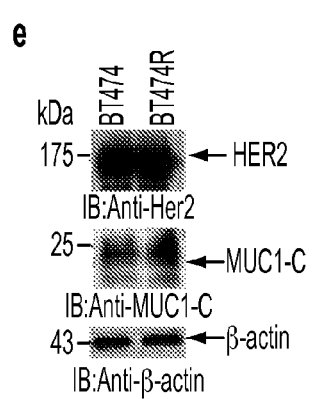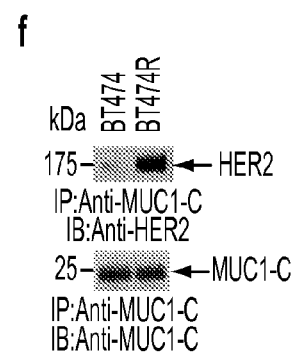
FIGS. 3A-F

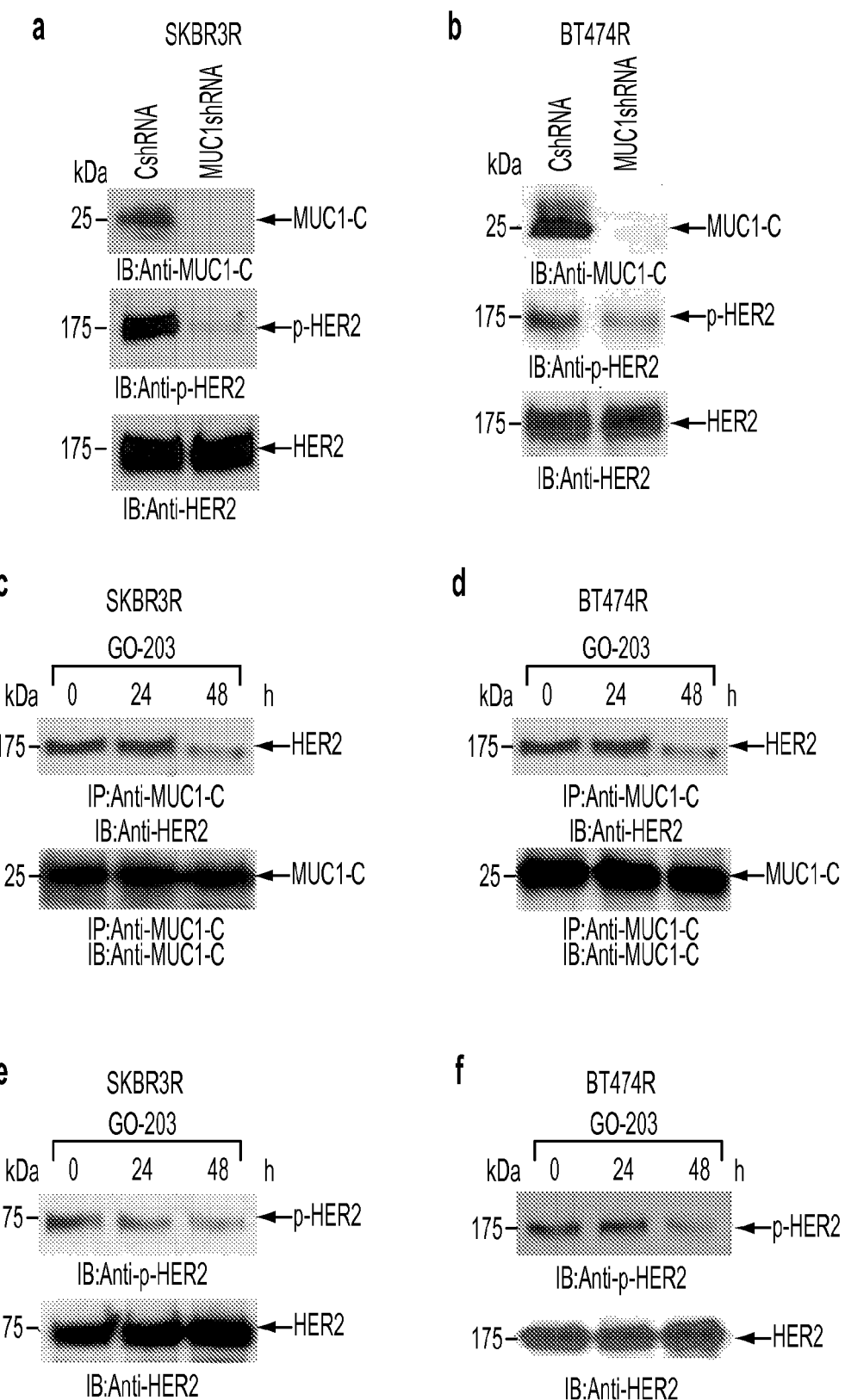
FIGS. 4A-F

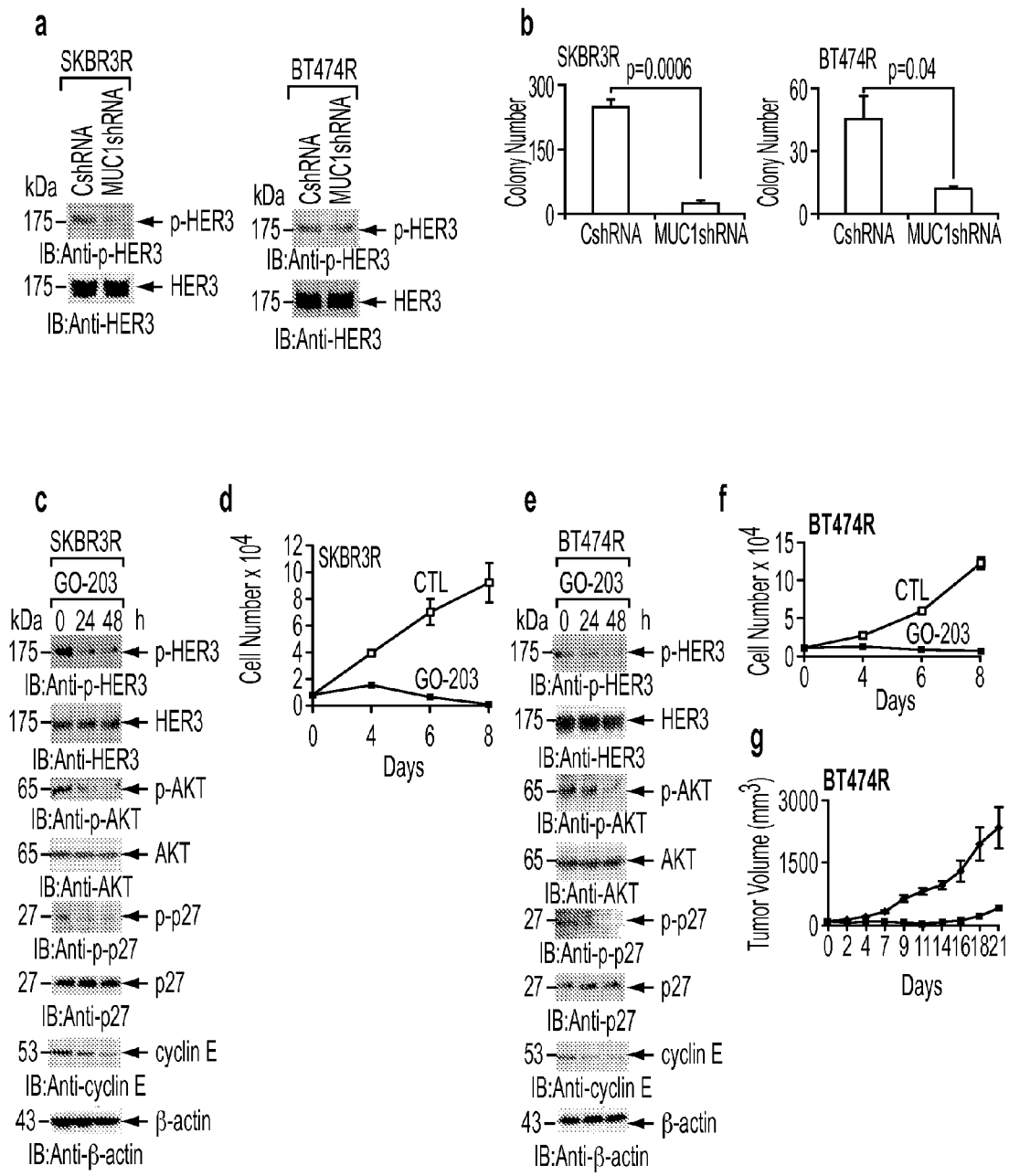
FIGS. 5A-F

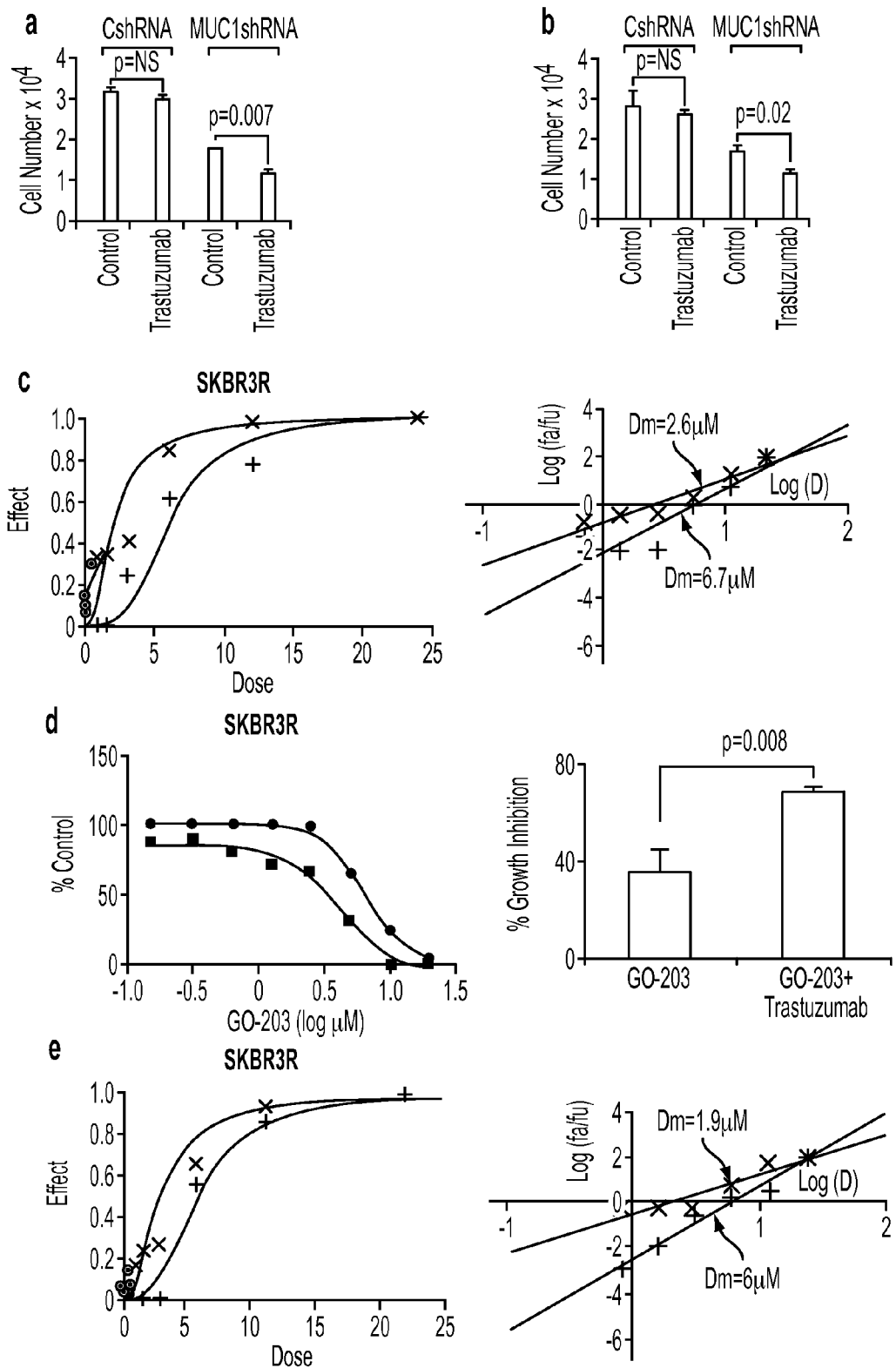
FIGS. 6A-E

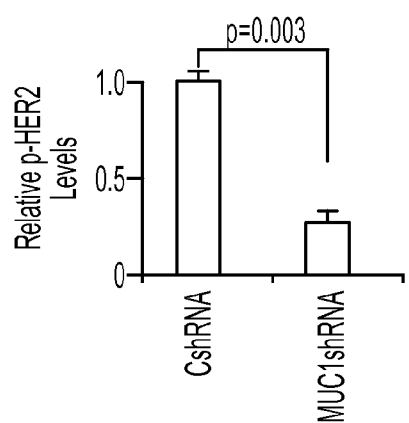
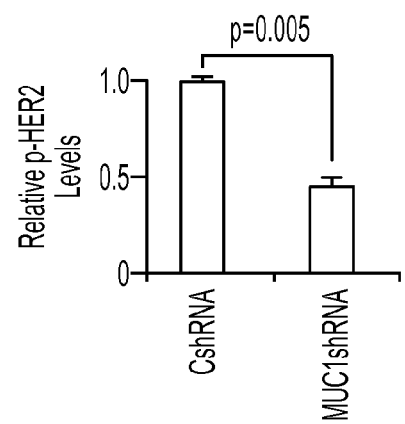
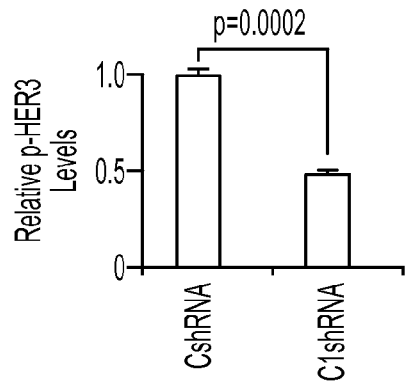
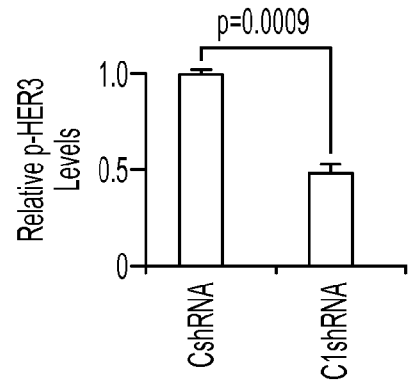
FIGS. 7A-D

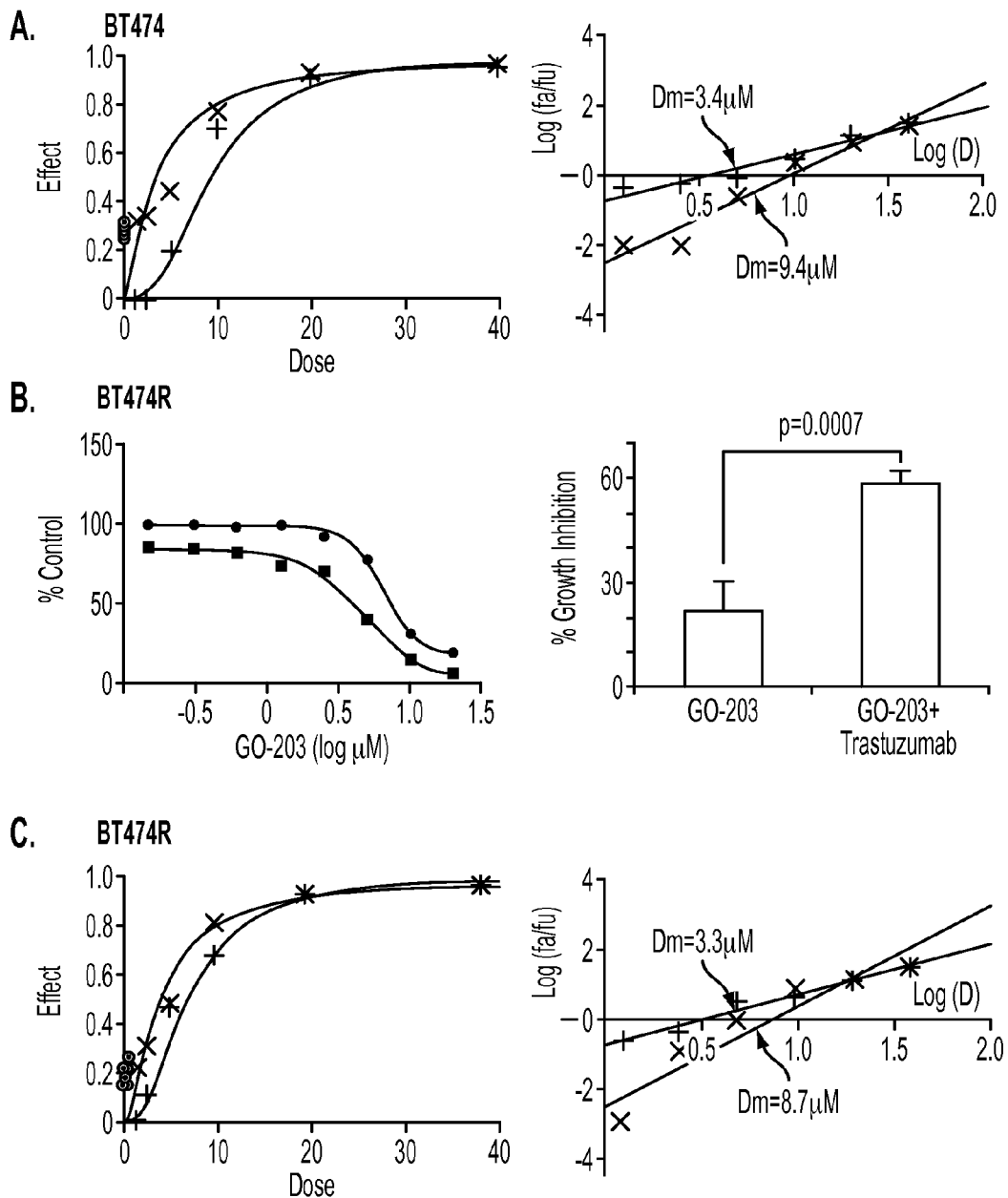
FIGS. 8A-C

A. SKBR3R
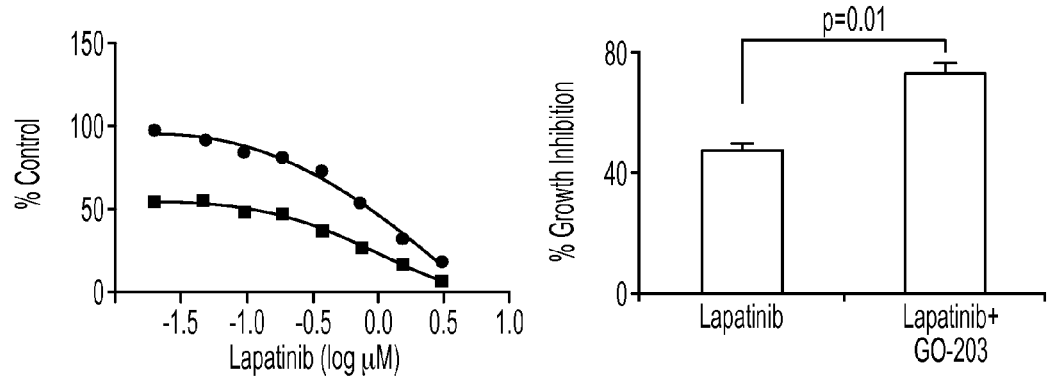
B. BT474R
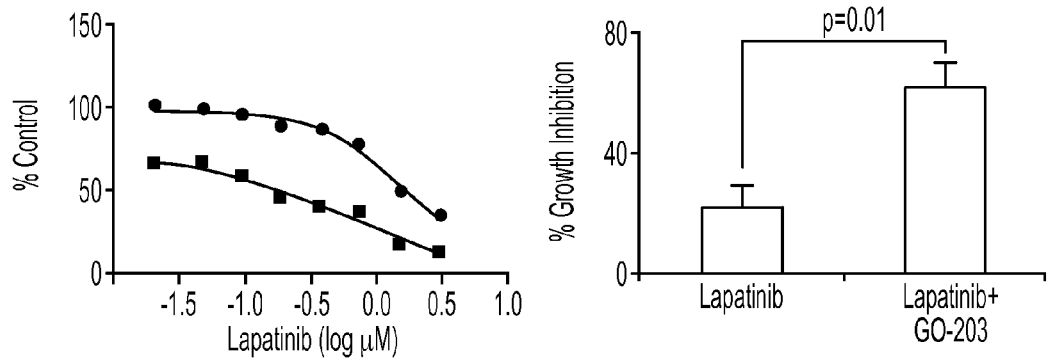
FIGS. 9A-C

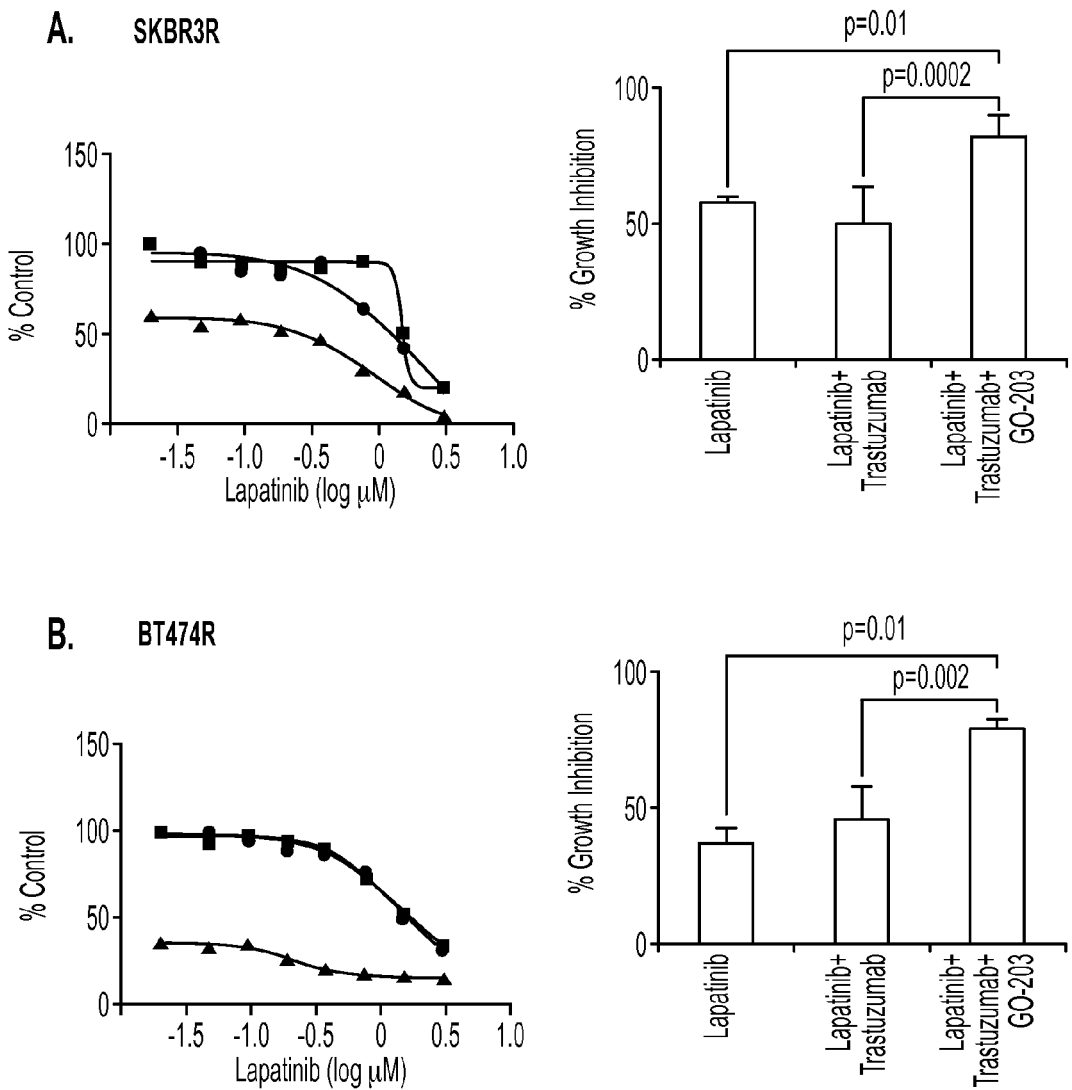
FIGS. 10A-B

SEQUENCE LISTING

```
<160> NUMBER OF SEQ ID NOS: 48

<210> SEQ ID NO 1
<211> LENGTH: 159
<212> TYPE: PRT
<213> ORGANISM: Homo sapiens

<400> SEQUENCE: 1

Gly Ser Val Val Gln Leu Thr Leu Ala Phe Arg Glu Gly Thr Ile
1               5                   10                  15

Asn Val His Asp Val Glu Thr Gln Phe Asn Gln Tyr Lys Thr Glu Ala
            20                  25                  30

Ala Ser Arg Tyr Asn Leu Thr Ile Ser Asp Val Ser Val Ser Asp Val
        35                  40                  45

Pro Phe Pro Phe Ser Ala Gln Ser Gly Ala Gly Val Pro Gly Trp Gly
    50                  55                  60

Ile Ala Leu Leu Val Leu Val Cys Val Leu Val Ala Leu Ala Ile Val
65                  70                  75                  80

Tyr Leu Ile Ala Leu Ala Val Cys Gln Cys Arg Arg Lys Asn Tyr Gly
                85                  90                  95

Gln Leu Asp Ile Phe Pro Ala Arg Asp Thr Tyr His Pro Met Ser Glu
                100                 105                 110
```

```
Tyr Pro Thr Tyr His Thr His Gly Arg Tyr Val Pro Ser Ser Thr
        115                 120                 125

Asp Arg Ser Pro Tyr Glu Lys Val Ser Ala Gly Asn Gly Gly Ser Ser
    130                 135                 140

Leu Ser Tyr Thr Asn Pro Ala Val Ala Ala Thr Ser Ala Asn Leu
145                 150                 155

<210> SEQ ID NO 2
<211> LENGTH: 72
<212> TYPE: PRT
<213> ORGANISM: Homo sapiens

<400> SEQUENCE: 2

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
            20                  25                  30

Gly Arg Tyr Val Pro Pro Ser Ser Thr Asp Arg Ser Pro Tyr Glu Lys
        35                  40                  45

Val Ser Ala Gly Asn Gly Gly Ser Ser Leu Ser Tyr Thr Asn Pro Ala
    50                  55                  60

Val Ala Ala Thr Ser Ala Asn Leu
65                  70

<210> SEQ ID NO 3
<211> LENGTH: 15
<212> TYPE: PRT
<213> ORGANISM: Homo sapiens

<400> SEQUENCE: 3

Cys Gln Cys Arg Arg Lys Asn Tyr Gly Gln Leu Asp Ile Phe Pro
1               5                   10                  15

<210> SEQ ID NO 4
<211> LENGTH: 3
<212> TYPE: PRT
<213> ORGANISM: Artificial Sequence
<220> FEATURE:
<223> OTHER INFORMATION: Synthetic peptide

<400> SEQUENCE: 4

Cys Gln Cys
1

<210> SEQ ID NO 5
<211> LENGTH: 34
<212> TYPE: PRT
<213> ORGANISM: Artificial Sequence
<220> FEATURE:
<223> OTHER INFORMATION: Synthetic peptide

<400> SEQUENCE: 5

Gln Ala Ala Thr Ala Thr Arg Gly Arg Ser Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 6
<211> LENGTH: 16
<212> TYPE: PRT
<213> ORGANISM: Artificial Sequence
```

```
<220> FEATURE:
<223> OTHER INFORMATION: Synthetic peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Arg Arg Met Lys Trp Lys Lys
1               5

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

Arg Arg Trp Arg Arg Trp Trp Arg Arg Trp Trp Arg Arg Trp Arg Arg
1               5                   10                  15

<210> SEQ ID NO 9
<211> LENGTH: 18
<212> TYPE: PRT
<213> ORGANISM: Artificial Sequence
<220> FEATURE:
<223> OTHER INFORMATION: Synthetic peptide

<400> SEQUENCE: 9

Arg Gly Gly Arg Leu Ser Tyr Ser Arg Arg Phe Ser Thr Ser Thr
1               5                   10                  15

Gly Arg

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10

Tyr Gly Arg Lys Lys Arg Arg Gln Arg Arg
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Arg Lys Lys Arg Arg Gln Arg Arg
1               5

<210> SEQ ID NO 12
<211> LENGTH: 11
<212> TYPE: PRT
```

```
<213> ORGANISM: Artificial Sequence
<220> FEATURE:
<223> OTHER INFORMATION: Synthetic peptide

<400> SEQUENCE: 12

Tyr Ala Arg Ala Ala Ala Arg Gln Ala Arg Ala
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Arg Arg Arg Arg Arg Arg Arg Arg
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide

<400> SEQUENCE: 14

Lys Lys Lys Lys Lys Lys Lys Lys
1               5

<210> SEQ ID NO 15
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(25)
<223> OTHER INFORMATION: Xaa can be any naturally occurring amino acid

<400> SEQUENCE: 15

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25

<210> SEQ ID NO 16
<211> LENGTH: 18
<212> TYPE: PRT
<213> ORGANISM: Artificial Sequence
<220> FEATURE:
<223> OTHER INFORMATION: Synthetic peptide

<400> SEQUENCE: 16

Leu Leu Ile Leu Leu Arg Arg Arg Ile Arg Lys Gln Ala Asn Ala His
1               5                   10                  15

Ser Lys

<210> SEQ ID NO 17
<211> LENGTH: 16
<212> TYPE: PRT
<213> ORGANISM: Artificial Sequence
<220> FEATURE:
<223> OTHER INFORMATION: Synthetic peptide

<400> SEQUENCE: 17
```

```
Ser Arg Arg His His Cys Arg Ser Lys Ala Lys Arg Ser Arg His His
1               5                   10                  15

<210> SEQ ID NO 18
<211> LENGTH: 11
<212> TYPE: PRT
<213> ORGANISM: Artificial Sequence
<220> FEATURE:
<223> OTHER INFORMATION: Synthetic peptide

<400> SEQUENCE: 18

Asn Arg Ala Arg Arg Asn Arg Arg Val Arg
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Arg Gln Leu Arg Ile Ala Gly Arg Arg Leu Arg Gly Arg Ser Arg
1               5                   10                  15

<210> SEQ ID NO 20
<211> LENGTH: 13
<212> TYPE: PRT
<213> ORGANISM: Artificial Sequence
<220> FEATURE:
<223> OTHER INFORMATION: Synthetic peptide

<400> SEQUENCE: 20

Lys Leu Ile Lys Gly Arg Thr Pro Ile Lys Phe Gly Lys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic peptide

<400> SEQUENCE: 21

Arg Arg Ile Pro Asn Arg Arg Pro Arg Arg
1               5                   10

<210> SEQ ID NO 22
<211> LENGTH: 17
<212> TYPE: PRT
<213> ORGANISM: Artificial Sequence
<220> FEATURE:
<223> OTHER INFORMATION: Synthetic peptide

<400> SEQUENCE: 22

Lys Leu Ala Leu Lys Leu Ala Leu Lys Ala Leu Lys Ala Ala Leu Lys
1               5                   10                  15

Leu

<210> SEQ ID NO 23
<211> LENGTH: 14
<212> TYPE: PRT
<213> ORGANISM: Artificial Sequence
<220> FEATURE:
<223> OTHER INFORMATION: Synthetic peptide
```

```
<400> SEQUENCE: 23

Lys Leu Ala Lys Leu Ala Lys Lys Leu Ala Lys Leu Ala Lys
1               5                   10

<210> SEQ ID NO 24
<211> LENGTH: 27
<212> TYPE: PRT
<213> ORGANISM: Artificial Sequence
<220> FEATURE:
<223> OTHER INFORMATION: Synthetic peptide

<400> SEQUENCE: 24

Gly Ala Leu Phe Leu Gly Phe Leu Gly Ala Ala Gly Ser Thr Asn Gly
1               5                   10                  15

Ala Trp Ser Gln Pro Lys Lys Lys Arg Lys Val
            20                  25

<210> SEQ ID NO 25
<211> LENGTH: 21
<212> TYPE: PRT
<213> ORGANISM: Artificial Sequence
<220> FEATURE:
<223> OTHER INFORMATION: Synthetic peptide

<400> SEQUENCE: 25

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 26
<211> LENGTH: 23
<212> TYPE: PRT
<213> ORGANISM: Artificial Sequence
<220> FEATURE:
<223> OTHER INFORMATION: Synthetic peptide

<400> SEQUENCE: 26

Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 27
<211> LENGTH: 23
<212> TYPE: PRT
<213> ORGANISM: Artificial Sequence
<220> FEATURE:
<223> OTHER INFORMATION: Synthetic peptide

<400> SEQUENCE: 27

Met Gly Leu Gly Leu His Leu Leu Val Leu Ala Ala Ala Leu Gln Gly
1               5                   10                  15

Ala Lys Ser Lys Arg Lys Val
            20

<210> SEQ ID NO 28
<211> LENGTH: 26
<212> TYPE: PRT
<213> ORGANISM: Artificial Sequence
<220> FEATURE:
<223> OTHER INFORMATION: Synthetic peptide

<400> SEQUENCE: 28
```

Ala Ala Val Ala Leu Leu Pro Ala Val Leu Leu Ala Leu Leu Ala Pro
1               5                   10                  15

Ala Ala Ala Asn Tyr Lys Lys Pro Lys Leu
            20                  25

<210> SEQ ID NO 29
<211> LENGTH: 28
<212> TYPE: PRT
<213> ORGANISM: Artificial Sequence
<220> FEATURE:
<223> OTHER INFORMATION: Synthetic peptide

<400> SEQUENCE: 29

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 30
<211> LENGTH: 24
<212> TYPE: PRT
<213> ORGANISM: Artificial Sequence
<220> FEATURE:
<223> OTHER INFORMATION: Synthetic peptide

<400> SEQUENCE: 30

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 31
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 31

Asp Pro Lys Gly Asp Pro Lys Gly Val Thr Val Thr Val Thr Val Thr
1               5                   10                  15

Val Thr Gly Lys Gly Asp Pro Xaa Pro Asp
            20                  25

<210> SEQ ID NO 32
<211> LENGTH: 14
<212> TYPE: PRT
<213> ORGANISM: Artificial Sequence
<220> FEATURE:
<223> OTHER INFORMATION: Synthetic peptide

<400> SEQUENCE: 32

Pro Pro Pro Pro Pro Pro Pro Pro Pro Pro Pro Pro Pro Pro
1               5                   10

<210> SEQ ID NO 33
<211> LENGTH: 18
<212> TYPE: PRT
<213> ORGANISM: Artificial Sequence
<220> FEATURE:
<223> OTHER INFORMATION: Synthetic peptide

```
<400> SEQUENCE: 33

Val Arg Leu Pro Pro Val Arg Leu Pro Pro Val Arg Leu Pro
1               5                   10                  15

Pro Pro

<210> SEQ ID NO 34
<211> LENGTH: 10
<212> TYPE: PRT
<213> ORGANISM: Artificial Sequence
<220> FEATURE:
<223> OTHER INFORMATION: Synthetic peptide

<400> SEQUENCE: 34

Pro Arg Pro Leu Pro Pro Pro Arg Pro Gly
1               5                   10

<210> SEQ ID NO 35
<211> LENGTH: 30
<212> TYPE: PRT
<213> ORGANISM: Artificial Sequence
<220> FEATURE:
<223> OTHER INFORMATION: Synthetic peptide

<400> SEQUENCE: 35

Ser Val Arg Arg Arg Pro Arg Pro Pro Tyr Leu Pro Arg Pro Arg Pro
1               5                   10                  15

Pro Pro Phe Phe Pro Pro Arg Leu Pro Pro Arg Ile Pro Pro
            20                  25                  30

<210> SEQ ID NO 36
<211> LENGTH: 21
<212> TYPE: PRT
<213> ORGANISM: Artificial Sequence
<220> FEATURE:
<223> OTHER INFORMATION: Synthetic peptide

<400> SEQUENCE: 36

Thr Arg Ser Ser Arg Ala Gly Leu Gln Phe Pro Val Gly Arg Val His
1               5                   10                  15

Arg Leu Leu Arg Lys
            20

<210> SEQ ID NO 37
<211> LENGTH: 23
<212> TYPE: PRT
<213> ORGANISM: Artificial Sequence
<220> FEATURE:
<223> OTHER INFORMATION: Synthetic peptide

<400> SEQUENCE: 37

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 38
<211> LENGTH: 37
<212> TYPE: PRT
<213> ORGANISM: Artificial Sequence
<220> FEATURE:
<223> OTHER INFORMATION: Synthetic peptide

<400> SEQUENCE: 38

Lys Trp Lys Leu Phe Lys Lys Ile Glu Lys Val Gly Gln Asn Ile Arg
```

-continued

```
                1               5                  10                 15
Asp Gly Ile Ile Lys Ala Gly Pro Ala Val Ala Val Val Gly Gln Ala
                20                 25                 30
Thr Gln Ile Ala Lys
        35

<210> SEQ ID NO 39
<211> LENGTH: 28
<212> TYPE: PRT
<213> ORGANISM: Artificial Sequence
<220> FEATURE:
<223> OTHER INFORMATION: Synthetic peptide

<400> SEQUENCE: 39

Ala Leu Trp Met Thr Leu Leu Lys Lys Val Leu Lys Ala Ala Ala Lys
1               5                   10                  15
Ala Ala Leu Asn Ala Val Leu Val Gly Ala Asn Ala
            20                  25

<210> SEQ ID NO 40
<211> LENGTH: 26
<212> TYPE: PRT
<213> ORGANISM: Artificial Sequence
<220> FEATURE:
<223> OTHER INFORMATION: Synthetic peptide

<400> SEQUENCE: 40

Gly Ile Gly Ala Val Leu Lys Val Leu Thr Thr Gly Leu Pro Ala Leu
1               5                   10                  15
Ile Ser Trp Ile Lys Arg Lys Arg Gln Gln
            20                  25

<210> SEQ ID NO 41
<211> LENGTH: 14
<212> TYPE: PRT
<213> ORGANISM: Artificial Sequence
<220> FEATURE:
<223> OTHER INFORMATION: Synthetic peptide

<400> SEQUENCE: 41

Ile Asn Leu Lys Ala Leu Ala Ala Leu Ala Lys Lys Ile Leu
1               5                   10

<210> SEQ ID NO 42
<211> LENGTH: 33
<212> TYPE: PRT
<213> ORGANISM: Artificial Sequence
<220> FEATURE:
<223> OTHER INFORMATION: Synthetic peptide

<400> SEQUENCE: 42

Gly Phe Phe Ala Leu Ile Pro Lys Ile Ile Ser Ser Pro Leu Pro Lys
1               5                   10                  15
Thr Leu Leu Ser Ala Val Gly Ser Ala Leu Gly Gly Ser Gly Gly Gln
            20                  25                  30
Glu

<210> SEQ ID NO 43
<211> LENGTH: 15
<212> TYPE: PRT
<213> ORGANISM: Artificial Sequence
<220> FEATURE:
<223> OTHER INFORMATION: Synthetic peptide
```

```
<400> SEQUENCE: 43

Leu Ala Lys Trp Ala Leu Lys Gln Gly Phe Ala Lys Leu Lys Ser
1               5                   10                  15

<210> SEQ ID NO 44
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(23)
<223> OTHER INFORMATION: Xaa can be any naturally occurring amino acid

<400> SEQUENCE: 44

Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
            20                  25

<210> SEQ ID NO 45
<211> LENGTH: 41
<212> TYPE: PRT
<213> ORGANISM: Artificial Sequence
<220> FEATURE:
<223> OTHER INFORMATION: Synthetic peptide

<400> SEQUENCE: 45

Leu Leu Gly Asp Phe Phe Arg Lys Ser Lys Glu Lys Ile Gly Lys Glu
1               5                   10                  15

Phe Lys Arg Ile Val Gln Arg Ile Lys Gln Arg Ile Lys Asp Phe Leu
            20                  25                  30

Ala Asn Leu Val Pro Arg Thr Glu Ser
            35                  40

<210> SEQ ID NO 46
<211> LENGTH: 20
<212> TYPE: PRT
<213> ORGANISM: Artificial Sequence
<220> FEATURE:
<223> OTHER INFORMATION: Synthetic peptide

<400> SEQUENCE: 46

Leu Lys Lys Leu Leu Lys Lys Leu Leu Lys Lys Leu Leu Lys Lys Leu
1               5                   10                  15

Leu Lys Lys Leu
            20

<210> SEQ ID NO 47
<211> LENGTH: 18
<212> TYPE: PRT
<213> ORGANISM: Artificial Sequence
<220> FEATURE:
<223> OTHER INFORMATION: Synthetic peptide

<400> SEQUENCE: 47

Lys Leu Lys Leu Lys Leu Lys Leu Lys Leu Lys Leu Lys Leu Lys Leu
1               5                   10                  15

Lys Leu

<210> SEQ ID NO 48
<211> LENGTH: 18
<212> TYPE: PRT
```

```
<213> ORGANISM: Artificial Sequence
<220> FEATURE:
<223> OTHER INFORMATION: Synthetic peptide

<400> SEQUENCE: 48

Pro Ala Trp Arg Lys Ala Phe Arg Trp Ala Trp Arg Met Leu Lys Lys
1               5                   10                  15

Ala Ala
```

COMBINATION ANTI-HUMAN EPIDERMAL GROWTH FACTOR RECEPTOR 2 (ANTI-HER2) CANCER THERAPY USING MUCIN 1 (MUC1) PEPTIDES AND HEMOTHERAPEUTICS

The application is a national phase application under 35 U.S.C. §371 of International Application No. PCT/US2014/022269, filed Mar. 10, 2014, which claims benefit of priority to U.S. Provisional Application Ser. No. 61/776,539, filed Mar. 11, 2013. The entire contents of the above-referenced disclosures are specifically incorporated herein by refrence.

BACKGROUND OF THE INVENTION

Pursuant to 37 C.F.R. 1.821(c), a sequence listing is submitted herewith as an ASCII compliant text file named "GENUP0035US_ST25.txt", created on Sep. 9, 2015 and having a size of ~16 kilobytes. The content of the aforementioned file is hereby incorporated by reference in its entirety.

1. Field of the Invention

This invention relates to regulation of cell growth, and more particularly to regulation of cancer cell growth. In particular, MUC1 peptides derived from a particular region of the MUC1 cytoplasmic domain have been shown to inhibit MUC oligomerization and nuclear translocation, causing inhibition and even death of MUC1-expressing tumor cells.

2. Related Art

The HER2/ERBB2 receptor tyrosine kinase (RTK) is overexpressed in approximately 20% of human breast cancers and is associated with aggressive disease and poor survival (Slamon et al., 1987 and Hynes et al., 2005). HER2 forms heterodimers with HER3 and thereby activates the PI3K->AKT pathway (Holbro et al., 2003). Downregulation of HER3 in HER2-dependent breast cancer cells is thus associated with inhibition of PI3K signaling and proliferation (Holbro et al., 2003). Trastuzumab is a humanized monoclonal antibody that binds to the HER2 extracellular domain and destabilizes ligand-independent HER2/HER3 complexes (Junttila et al., 2009). Targeting of HER2 with trastuzumab in HER2-overexpressing breast cancer cells also suppresses constitutive activation of the PI3K->AKT pathway (Junttila et al., 2009), decreases HER2 levels (Klapper et al., 2000 and Scaltriti et al., 2009), and induces GI1 arrest by stabilizing the CDK inhibitor p27 (Shin et al., 2002). Trastuzumab extends the overall survival of certain patients with HER2-overexpressing breast cancers when used as monotherapy or in combination with chemotherapy (Slamon et al., 2001, Romond et al., 2005 and Spector and Blackwell, 2009). However, many patients exhibit de novo unresponsiveness to trastuzumab or develop acquired resistance after treatment (Spector and Blackwell, 2009). Trastuzumab resistance has been associated with constitutive activation of the PI3K pathway as a result of phosphatase and tensin homolog (PTEN) deficiency (Nagata et al., 2004) or PIK3CA gene mutations (Berns et al., 2007). PTEN has also been linked to SRC activation and thereby trastuzumab resistance in breast cancer cells and in breast tumors (Zhang et al., 2011). Additional mechanisms of resistance have included expression of a truncated p95HER2 that lacks the trastuzumab binding domain (Scaltriti et al., 2007), heterodimerization with other RTKs (Nahta et al. 2005, Shattuck et al., 2008 and Huang et al., 2010) and downregulation of HER2 expression (Mittendorf et al., 2009). Other studies have shown that resistance of HER2-overexpressing breast cancer cells to trastuzumab is conferred by (i) upregulation of cyclin E and an increase in CDK2 activity (Scaltriti et al., 2011), and (ii) decreased expression of the PPM1H phosphatase that regulates p27 stability (Nahta et al., 2004 and Lee-Hoeflich et al., 2011). These findings have provided the experimental basis for designing trials that target pathways associated with trastuzumab resistance to reverse unresponsiveness to this agent in the clinic.

MUC1 is a heterodimeric protein that constitutively associates with HER2 on the surface of breast cancer cells (Li et al., 2003 and Kufe, 2013). MUC is translated as a single polypeptide that undergoes autocleavage into N-terminal (MUC1-N) and C-terminal (MUC1-C) fragments, which in turn form a stable complex at the cell membrane (Kufe, 2009). The MUC1-N/MUC1-C heterodimer is positioned at the apical border of breast epithelial cells and is sequestered from RTKs that are expressed at the baso-lateral membranes (Kufe, 2013 and Kufe, 2009). However, with loss of apical-basal polarity as a result of stress or transformation, MUC1 is repositioned over the entire cell membrane and interacts with RTKs such as HER2 (Li et al., 2003, Kufe, 2013 and Kufe, 2009). MUC1-N, the mucin component of the heterodimer, is shed from the cell surface (Kufe, 2013 and Kufe, 2009). The MUC1-C subunit spans the cell membrane and includes a 58 amino acid (aa) extracellular domain, a 28 as transmembrane domain and a 72 as cytoplasmic domain. MUC1-C associates with RTKs through extracellular galectin-3 bridges (Duraisamy et al., 2007). In addition, the MUC1-C cytoplasmic domain functions as a substrate for phosphorylation by RTKs and SRC (Kufe, 2013 and Kufe, 2009). The MUC1-C cytoplasmic domain also contains a YHPM motif that, when phosphorylated on tyrosine, functions as a binding site for PI3K p85 SH2 domains (Raina et al., 2011). Overexpression of MUC1-C, as found in breast cancers, is associated with activation of the PI3K→AKT pathway (Raina et al., 2004). These findings and the demonstration that MUC1-C overexpression is sufficient to induce anchorage-independent growth and tumorigenicity (Li et al., 2003 and Huang et al., 2005) provided the basis for developing agents that block the MUC1-C transforming function (Kufe, 2009). In this respect, the MUC1-C cytoplasmic domain contains a CQC motif that is necessary for its dimerization and function (Leng et al., 2007). Accordingly, cell-penetrating peptides that bind to the MUC1-C CQC motif are effective in inhibiting growth and inducing death of human breast cancer cells growing in vitro and as xenografts in mice (Raina et al., 2009). MUC1-C inhibitors were also found to be effective in (i) blocking the interaction between the MUC1-C cytoplasmic domain and PI3K p85 in vitro, and (ii) suppressing constitutive activation of the PI3K→AKT pathway in cells (26). However, the effects of MUC1-C inhibition on (i) the interaction between MUC1-C and HER2, and (ii) HER2 signaling in breast cancer cells are not known.

SUMMARY OF THE INVENTION

Thus, in accordance with the present invention, there is provided a method of inhibiting a MUC1-positive/HER2-positive tumor cell in a subject comprising administering to said subject a MUC1 peptide of at least 4 consecutive MUC1 residues and no more than 20 consecutive MUC1 residues and comprising the sequence CQC (SEQ ID NO:4), wherein the amino-terminal cysteine of CQC is covered on its $NH_2$-terminus by at least one amino acid residue that need not correspond to the native MUC-1 transmembrane sequence, wherein said tumor cell exhibits primary resistance to trastuzamab. The method may further comprise the step of assessing the expression of MUC1 in a tumor cell of said subject prior to administering said peptide. The method may further comprise the step of assessing the expression of HER2 in a tumor cell of said subject prior to administering said peptide. The subject may have metastatic and/or recurrent cancer. HER2 may be overexpressed as compared to a similar non-cancerous cell. The peptide may be formulated with a nanoparticle.

Administering may comprise intravenous, intra-arterial, intra-tumoral, subcutaneous, topical or intraperitoneal administration, or may comprise local, regional, systemic, or continual administration. Inhibiting may comprise inducing growth arrest of said tumor cell, apoptosis of said tumor cell and/or necrosis of a tumor tissue comprising said tumor cell. The method may further comprise administering to said subject an anti-HER2 therapy, such as trastuzumab, pertuzumab or lapatinab. The anti-HER2 therapy may be administered prior to the peptide, after said peptide, or at the same time as said peptide. The subject may be a human. The peptide may be administered at 0.1-500 mg/kg/d or at 10-100 mg/kg/d. The peptide may be administered daily, such as daily for 7 days, 2 weeks, 3 weeks, 4 weeks, one month, 6 weeks, 8 weeks, two months, 12 weeks, or 3 months. The peptide may be administered weekly, such as weekly for 2 weeks, 3 weeks, 4 weeks, 6 weeks, 8 weeks, 10 weeks, or 12 weeks.

The peptide may comprise all L amino acids, all D amino acids, or a mix of L and D amino acids. The peptide may comprise at least 5, 6, 7 or 8 consecutive MUC1 residues, and/or may contain no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1. The MUC1-positive tumor cell may be a breast carcinoma cellor a prostate carcinoma cell. The peptide may be fused to a cell delivery domain, such as poly-D-R, poly-D-P or poly-D-K. The peptide may be at least 8 residues in length, and at least two non-adjacent residues form a bridge through their side chains. The bridge may comprise a linker, chemically modified side chains, or hydrocarbon stapling. The linker may comprise a modification that stabilizes an alpha-helical structure of said peptide. The cancer cell may be a carcinoma cell, a leukemia cell or a myeloma cell. The carcinoma cell may be a prostate or breast carcinoma cell.

In another embodiment, there is provided a method of treating a human subject having MUC1-positive/HER2-positive cancer comprising administering to said subject (a) a MUC peptide of at least 4 consecutive MUC residues and no more than 20 consecutive MUC1 residues and comprising the sequence CQC (SEQ ID NO:4), wherein the amino-terminal cysteine of CQC is covered on its $NH_2$-terminus by at least one amino acid residue that need not correspond to the native MUC-1 transmembrane sequence; and (b) an anti-HER2 therapy. The anti-HER2 therapy may be trastuzumab, pertuzumab or lapatinab. The MUC1 peptide and/or said anti-HER2 therapy may be administered to said subject more than once. The subject may have previously received an anti-HER2 therapy, or not previously received an anti-HER2 therapy. The cancer may be recurrent and/or metastatic. The HER2 may be overexpressed as compared to a similar non-cancerous cell. The method may improve the response rate to said anti-HER2 therapy as compared to the anti-HER2 therapy given alone, or reverses resistance to said anti-HER2 therapy.

The cancer may be is a carcinoma, such as gastric, prostate or breast carcinoma. The anti-HER2 therapy may be administered prior to said peptide, after said peptide or at the same time as said peptide. The method may further comprise the step of assessing the expression of MUC1 in a tumor cell of said subject prior to administering said peptide. The method may further comprise the step of assessing the expression of HER2 in a tumor cell of said subject prior to administering said peptide. The peptide may be formulated with a nanoparticle.

In yet another embodiment, there is provided a method of inhibiting a MUC1-positive/HER2-positive tumor cell in a subject comprising administering to said subject a MUC1 peptide of at least 4 consecutive MUC1 residues and no more than 20 consecutive MUC1 residues and comprising the sequence CQC (SEQ ID NO:4), wherein the amino-terminal cysteine of CQC is covered on its $NH_2$-terminus by at least one amino acid residue that need not correspond to the native MUC-1 transmembrane sequence, wherein said tumor cell exhibits acquired resistance to trastuzamab. The subject may be a human. The method may further comprise the step of assessing the expression of MUC1 in a tumor cell of said subject prior to administering said peptide. The method may further comprise the step of assessing the expression of HER2 in a tumor cell of said subject prior to administering said peptide. The subject may have metastatic and/or recurrent cancer. HER2 may be overexpressed as compared to a similar non-cancerous cell.

The peptide may comprise at least 5, 6, 7 or 8 consecutive MUC1 residues, and/or may contain no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1. The MUC1-positive tumor cell may be a carcinoma cell, a leukemia cell or a myeloma cell. The carcinoma cell may be a prostate or breast carcinoma cell. The peptide may be is fused to a cell delivery domain, such as poly-D-R, poly-D-P or poly-D-K. The peptide may be administered at 0.1-500 mg/kg/d, or at 10-100 mg/kg/d. The peptide may comprise all L amino acids, all D amino acids, or a mix of L and D amino acids. The peptide may be at least 8 residues in length, and at least two non-adjacent residues form a bridge through their side chains. The bridge may comprise a linker, chemically modified side chains, or hydrocarbon stapling. The linker may comprise a modification that stabilizes an alpha-helical structure of said peptide. The peptide may be formulated with a nanoparticle.

Administering may comprise intravenous, intra-arterial, intra-tumoral, subcutaneous, topical or intraperitoneal administration, or administering may comprise local, regional, systemic, or continual administration. Inhibiting may comprise inducing growth arrest of said tumor cell, apoptosis of said tumor cell and/or necrosis of a tumor tissue comprising said tumor cell. The method may further comprise administering to said subject an anti-HER2 therapy, such as trastuzumab, pertuzumab or lapatinab. The anti-HER2 therapy may be administered prior to said peptide, after said peptide, or at the same time as said peptide. The peptide may be administered daily, such as daily for 7 days, 2 weeks, 3 weeks, 4 weeks, one month, 6 weeks, 8 weeks, two months, 12 weeks, or 3 months. The peptide may be administered weekly, such as weekly for 2 weeks, 3 weeks, 4 weeks, 6 weeks, 8 weeks, 10 weeks, or 12 weeks. The cancer cell may be a carcinoma cell, a leukemia cell or a myeloma cell. The carcinoma cell may be a prostate or breast carcinoma cell.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed.

FIGS. 1A-E. Silencing MUC1-C downregulates HER2 activation and colony formation. (FIG. 1A) Lysates from SKBR3 and BT474 cells were immunoblotted (IB) with the indicated antibodies. (FIG. 1B) Lysates from SKBR3 (left) and BT474 (right) cells were precipitated with anti-MUC1-C or a control immunoglobulin G (IgG). The precipitates were immunoblotted with the indicated antibodies. (FIG. 1C). SKBR3 (left) and BT474 (right) cells were infected with lentiviruses to stably express a control shRNA (CshRNA) or a MUC1shRNA. Lysates were immunoblotted with the indicated antibodies. (FIG. 1D) The indicated SKBR3 (left) and BT474 (right) cells were seeded at $5 \times 10^4$ cells per well. The results (mean±s.d. of three replicates) are expressed as the cell number on day 4. (FIG. 1E) The indicated SKBR3 (left) and BT474 (right) cells were seeded at 2000 and 1000 cells per well, respectively, and incubated for 12 days. Colony number is expressed as the mean±s.d. of three replicates. IP, immunoprecipitated.

FIGS. 2A-F. Targeting the MUC1-C CD with GO-203 blocks the interaction with HER2 and suppresses HER2 activation. (FIG. 2A) Schema of the MUC1-C subunit with the 58-aa extracellular domain (ED), the 28-aa transmembrane domain (TM) and the amino-acid sequence of the 72-aa CD. Highlighted is the CQC motif that is necessary and sufficient for dimerization of the MUC1-C subunit. Lysates from SKBR3 (left) and BT474 (right) cells were incubated with the indicated GST or GST-fusion proteins. The adsorbates were immunoblotted (IB) with anti-HER2. Input of the GST proteins was assessed by Coomassie blue staining. (FIG. 2B) D-Amino-acid sequences of the GO-203 and CP-2 peptides. SKBR3 (left) and BT474 (right) cells were treated with 5 mM GO-203 or CP-2 for 48 h. Anti-MUC1-C precipitates were immunoblotted with anti-HER2 and anti-MUC1-C. (FIG. 2C) SKBR3 cells were treated with 5 mM GO-203 or CP-2 for 48 h (left) or with 5 mM GO-203 for the indicated times (right). Lysates were immunoblotted with the indicated antibodies. (FIG. 2D) BT474 cells were treated with 5 mM GO-203 or CP-2 for 48 h. Lysates were immunoblotted with the indicated antibodies. (FIGS. 2E-F) SKBR3 (FIG. 2E) and BT474 (FIG. 2F) cells were left untreated (Control; CTL) or treated with 5 mM GO-203 for the indicated times. Cell number (mean±s.e. of three determinations) was determined by Trypan blue staining. IP, immunoprecipitated.

FIGS. 3A-F. Interaction between MUC1-C and HER2 is upregulated in trastuzumab-resistant breast cancer cells. (FIG. 3A) SKBR3 (left) and SKBR3R (right) cells ($1 \times 10^4$ per well) were left untreated or treated with 80 nM trastuzaumb for 72 h. Cell number (mean±s.e. of three determinations) was determined by Trypan blue staining. (FIG. 3B) Lysates from SKBR3 and SKBR3R cells were immunoblotted (IB) with the indicated antibodies. (FIG. 3C) Anti-MUC1-C precipitates from SKBR3 and SKBR3R cells were immunoblotted with the indicated antibodies. (FIG. 3D) BT474 (left) and BT474R (right) cells ($1 \times 10^4$ per well) were left untreated or treated with 80 nM trastuzumab for 72 h. Cell number (mean±s.e. of three determinations) was determined by Trypan blue staining. (FIG. 3E) Lysates from BT474 and BT474R cells were immunoblotted with the indicated antibodies. (FIG. 3F) Anti-MUC1-C precipitates from BT474 and BT474R cells were immunoblotted with the indicated antibodies. IP, immunoprecipitated.

FIGS. 4A-F. Downregulation of MUC1-C suppresses HER2 activation in trastuzumab-resistant cells. (FIGS. 4A-B) SKBR3R (FIG. 4A) and BT474R (FIG. 4B) cells were infected with lentiviruses expressing a control shRNA (CshRNA) or MUC1shRNA. Lysates were immunoblotted (IB) with the indicated antibodies. (FIGS. 4C-D) SKBR3R (FIG. 4C) and BT474R (FIG. 4D) cells were treated with 5 mM GO-203 for the indicated times. Anti-MUC1-C precipitates were immunoblotted with the indicated antibodies. (FIGS. 4E-F) SKBR3R (FIG. 4E) and BT474R (FIG. 4F) cells were treated with 5 mM GO-203 for the indicated times. Lysates were immunoblotted with the indicated antibodies. IP, immunoprecipitated.

FIGS. 5A-G. Targeting MUC1-C in trastuzumab-resistant cells suppresses HER3 activation and inhibits growth and clonogenic survival. (FIG. 5A) Lysates from the indicated SKBR3R (left) and BT474R (right) cells were immunoblotted (IB) with anti-p-HER3 and anti-HER3. (FIG. 5B) The indicated SKBR3R (left) and BT474R (right) cells were seeded at 4000 and 1000 cells per well, respectively, and incubated for 12 days. The colony number is expressed as the mean±s.e. of three replicates. (FIG. 5C) SKBR3R cells were treated with 5 mM GO-203 for the indicated times. Lysates were immunoblotted with the indicated antibodies. (FIG. 5D) SKBR3R cells were left untreated (Control; CTL) or treated with 5 mM GO-203 for the indicated times. Cell number (mean±s.e. of three determinations) was determined by Trypan blue staining. (FIG. 5E) BT474R cells were treated with 5 mM GO-203 for the indicated times. Lysates were immunoblotted with the indicated antibodies. (FIG. 5F) BT474R cells were left untreated (Control; CTL) or treated with 5 mM GO-203 for the indicated times. Cell number (mean±s.e. of three determinations) was determined by Trypan blue staining. (FIG. 5G) BALB/c nu/nu mice were injected subcutaneously in the flank with 1_107 BT474R cells. The mice were pair-matched when the tumors were 80-100 mm3. Treatment groups consisted of eight mice injected intravenously with phosphate-buffered saline (vehicle control; diamonds) or 7.5 mg/kg GO-203 (squares) each day for 21 days. There was no weight loss in the two groups. The results are expressed as tumor volume (mean±s.e. for the eight mice in each group).

FIGS. 6A-E. Targeting MUC1-C reverses trastuzaumab resistance. (a and b) The indicated SKBR3R (a) and BT474R (b) cells (1_104 per well) were left untreated or treated with 80 nM trastuzumab for 72 h. Cell number (mean±s.e. of three determinations) was assessed by Trypan blue staining. (c) SKBR3 cells were treated with GO-203 alone (♭), trastuzumab alone (♮) and the combination (X) based on the IC50 values listed in Table 1A. Growth inhibition data were analyzed by the method of Chou and Talalay using the CalcuSyn program. The dose-effect curves (left) and median-effect plots (right) are shown using mM concentrations for GO-203 and trastuzumab. The CI values are listed in Table 1B. (d) SKBR3R cells were treated with GO-203 alone (closed circles) and in combination with 40 nM trastuzumab (closed squares) for 72 h. Growth inhibition plots (left) were generated by Prism GraphPad software and the BI score (Table 2) was calculated as described in the Materials and methods. The percentage growth inhibition (mean±s.e. of three determinations) obtained with 5 mM GO-203 was significantly different from that with 5 mM GO-203♭40 nM trastuzumab (right). (e) SKBR3R cells were treated with GO-203 alone (♭), trastuzumab alone (♮) and the combination (X). Growth inhibition data were analyzed by the method of Chou and Talalay using the CalcuSyn program. The dose-effect curves (left) and median-effect plots (right) are shown using mM concentrations for GO-203 and trastuzumab. The CI values are listed in Table 1B. NS, nonsignificant.

FIGS. 7A-D. Silencing MUC1-C decreases p-HER2 and p-HER3 levels. (FIGS. 7A-B). Densitometric scanning of the p-HER2 signals in SKBR3R (FIG. 7A) and BT474R (FIG. 7B) cells demonstrated that silencing MUC1 is associated with a 74% and 45% decrease in p-HER2 levels (mean±SE of three determinations), respectively. (FIGS. 7C-D (. Densitometric scanning of the p-HER3 signals in SKBR3R (FIG. 7C) and BT474R (FIG. 7D) cells demonstrated that silencing MUC1 is associated with a 55% and 52% decrease in p-HER3 levels (mean±SE of three determinations), respectively.

FIGS. 8A-C. Synergy of GO-203 and trastuzumab in the treatment of BT474 and BT474R cells. (FIG. 8A) BT474 cells were treated with GO-203 alone (+), trastuzumab alone (⊚), and the combination (X) based on the $IC_{50}$ values listed in Table 1A. Growth inhibition data were analyzed by the method of Chou and Talalay using the CalcuSyn program. The dose-effect curves (left) and median-effect plots (right) are shown using μM concentrations for GO-203 and trastuzumab. The CI values are listed in Table IB. (FIG. 8B) BT474R cells were treated with GO-203 alone (circles) and in combination with 40 nM trastuzumab (squares) for 72 h. Growth inhibition plots (left) were generated by Prism GraphPad software and the BI score was calculated as described in the Materials and Methods (Table 2). The percentage growth inhibition (mean±SE of three determinations) obtained with 5 μM GO-203 was significantly different from that with 5 μM GO-203+40 nM trastuzumab (right). (FIG. 8C) BT474R cells were treated with GO-203 alone (+), trastuzumab alone (⊚), and the combination (X). Growth inhibition data were analyzed by the method of Chou and Talalay using the CalcuSyn program. The dose-effect curves (left) and median-effect plots (right) are shown using μM concentrations for GO-203 and trastuzumab. The CI values are listed in Table 1B.

FIGS. 9A-B. Effects of combining lapatinib with GO-203 in the treatment of trastuzumab-resistant cells. SKBR3R (FIG. 9A) and BT474R (FIG. 9B) cells were treated with the indicated lapatinib concentrations alone (circles) or in combination with 4 μM GO-203 (squares) for 72 h. Growth inhibition plots (left) were generated by Prism GraphPad software (left) and the BI score was calculated as described in the Materials and Methods (Table 3). The percentage growth inhibition (mean±SE of three determinations) obtained with 0.75 μM lapatinib was significantly different from that with 0.75 μM lapatinib+4 μM GO-203 (right).

FIGS. 10A-B. SKBR3R (FIG. 10A) and BT474R (FIG. 10B) cells were treated with the indicated lapatinib concentrations alone (circles), in combination with 40 nM trastuzumab (squares) or in combination with 40 nM trastuzumab+4 μM GO-203 (triangles) for 72 h. Growth inhibition plots (left) were generated by Prism GraphPad software (left) and the BI score was calculated as described in the Materials and Methods (Table 4). The percentage growth inhibition (mean±SE of three determinations) obtained with 1.5 μM lapatinib was significantly different from that with 1.5 μM lapatinib+40 nM trastuzumab+4 μM GO-203 (right).

DESCRIPTION OF ILLUSTRATIVE EMBODIMENTS

In 2006, the inventors reported that MUC1 is imported into the nucleus by a mechanism involving binding to Nup62. They also demonstrated that MUC forms oligomers through a CQC motif in the MUC1 cytoplasmic domain and that MUC1 oligomerization is necessary for nuclear import. In 2009, they extended this work to encompass a further understanding of the role that the CQC motif plays in oligomer formation. They demonstrated that short peptides corresponding to this region are able to disrupt MUC1 oligomer formation, preventing transport into the nucleus of tumor cells. These peptides were able to inhibit tumor cell growth, as well as induce apoptosis in such cells and even necrosis of tumor tissue.

Now, the inventors show that one of the in studies on HER2-overexpressing breast cancer cells, the formation of MUC1-C/HER2/HER3 complexes is substantially increased in the setting of trastuzumab resistance. They also show that MUC1-C inhibition is associated with disruption of MUC1-C/HER2/HER3 complexes, downregulation of HER2/HER3 activation and suppression of PI3K->AKT signaling. In concert with these findings, direct inhibition of the MUC1-C cytoplasmic domain was effective in reversing trastuzumab resistance. These and other aspects of the invention are described in detail below.

I. MUC1

A. Structure

MUC1 is a mucin-type glycoprotein that is expressed on the apical borders of normal secretory epithelial cells (Kufe et al., 1984). MUC1 forms a heterodimer following synthesis as a single polypeptide and cleavage of the precursor into two subunits in the endoplasmic reticulum (Ligtenberg et al., 1992). The cleavage may be mediated by an autocatalytic process (Levitan et al., 2005). The >250 kDa MUC1 N-terminal (MUC1 N-ter, MUC1-N) subunit contains variable numbers of 20-amino acid tandem repeats that are imperfect with highly conserved variations and are modified by O-linked glycans (Gendler et al., 1988; Siddiqui et al., 1988). MUC1-N is tethered to the cell surface by dimerization with the ~23 kDa C-terminal subunit (MUC1C-ter, MUC1-C), which includes a 58-amino acid extracellular region, a 28-amino acid transmembrane domain and a 72-amino acid cytoplasmic domain (CD; SEQ ID NO:1) (Merlo et al., 1989). The human MUC1 sequence is shown below:

GSVVVQLTLAFREGTINVHDVETQFNQYKTEAASRYNLTISDVSVSDVP

FPFSAQSGAGVPGWGIALLVLVCVLVALAIVYLIALAVCQCRRKNYGQL

DIFPARDTYHPMSEYPTYHTHGRYVPPSSTDRSPYEKVSAGNGGSSLSY

TNPAVAATSANL

The bold sequence indicates the CD (SEQ ID NO: 2), and the underlined portion is an oligomer-inhibiting peptide (SEQ ID NO:3) described in the examples.

With transformation of normal epithelia to carcinomas, MUC is aberrantly overexpressed in the cytosol and over the entire cell membrane (Kufe et al., 1984; Perey et al., 1992). Cell membrane-associated MUC1 is targeted to endosomes by clathrin-mediated endocytosis (Kinlough et al., 2004). In addition, MUC1-C, but not MUC1-N, is targeted to the nucleus (Baldus et al., 2004; Huang et al., 2003; Li et al., 2003a; Li et al., 2003b; Li et al., 2003c; Wei et al., 2005; Wen et al., 2003) and mitochondria (Ren et al., 2004).

II. HER2-Expressing and -Overexpressing Cancers

HER2 (Human Epidermal Growth Factor Receptor 2) also known as Neu, ErbB-2, CD340 (cluster of differentiation 340) or p185, is a protein that in humans is encoded by the ERBB2 gene. HER2 is a member of the epidermal growth factor receptor (EGFR/ErbB) family. Amplification or over-expression of this gene has been shown to play an important role in the pathogenesis and progression of certain aggressive types of breast cancer and in recent years it has evolved to become an important biomarker and target of therapy for the disease.

The ErbB family is composed of four plasma membrane-bound receptor tyrosine kinases. All four contain an extracellular ligand binding domain, a transmembrane domain, and an intracellular domain that can interact with a multitude of signaling molecules. Unlike the other family members, HER2 is considered to be an orphan receptor as it has no known ligand. However, all of the other three ErbB receptors have known ligands and will form either homodimers or heterodimers upon ligand binding. HER2 can heterodimerise with any of the other three receptors and is considered to be the preferred dimerisation partner of the other ErbB receptors. Dimerisation results in the autophosphorylation of tyrosine residues within the cytoplasmic domain of the receptors and initiates a variety of signaling pathways.

Amplification or over-expression of the ERBB2 gene occurs in approximately 30% of breast cancers. It is strongly associated with increased disease recurrence and a worse prognosis. Overexpression is also known to occur in ovarian, stomach, and aggressive forms of uterine cancer, such as uterine serous endometrial carcinoma. HER2 is co-localized, and, most of the time, co-amplified with the gene GRB7, which is a proto-oncogene associated with breast, testicular germ cell, gastric, and esophageal tumors. HER2 proteins have been shown to form clusters in cell membranes that may play a role in tumorigenesis.

HER2 is the target of the monoclonal antibody trastuzumab (marketed as Herceptin®). Trastuzumab is effective only in cancers where HER2 is over-expressed. An important downstream effect of trastuzumab binding to HER2 is an increase in p27, a protein that halts cell proliferation. If the cancer does not overexpress HER2 receptors, trastuzumab will have no beneficial effect, and may in fact be harmful. Routine HER-2 status is performed by IHC, there are two FDA-approved commercial kits available; Dako HercepTest and Ventana Pathway®.

The majority of HER2+ cancers fail to respond at all to trastuzumab, and most of those that do respond become resistant to the drug within a year. There are a number of possible explanations for resistance, such as (i) impaired trastuzumab binding to HER2 (truncated HER2 and epitope masking); (ii) upregulation of HER2 downstream signaling pathways (PTEN loss, increased PI3K/Akt activity and PDK1 changes); (iii) alternative signaling pathways (increased signaling from HER family and other receptors); and (d) impaired immune-mediated mechanisms. Whatever the cause may be, the incidence of resistance greatly limits the clinical impact of this antibody.

Another monoclonal antibody, Pertuzumab, which inhibits dimerization of HER2 and HER3 receptors, was approved by the FDA for use in combination with trastuzumab in June 2012. Additionally, NeuVax (Galena Biopharma) is a peptide-based immunotherapy that directs killer T cells to target and destroy cancer cells that express HER2. It has entered phase 3 clinical trials. It is now thought that patients with ER+/HER2+ compared with ER−/HER2+ breast cancers may actually benefit more from drugs that inhibit the PI3K/AKT molecular pathway.

Over-expression of HER2 can also be suppressed by the amplification of other genes. Research is currently being conducted to discover which genes may have this desired effect. The expression of HER2 is regulated by signaling through estrogen receptors. Normally, estradiol and tamoxifen acting through the estrogen receptor down-regulate the expression of HER2. However, when the ratio of the coactivator AIB-3 exceeds that of the corepressor PAX2, the expression of HER2 is upregulated in the presence of tamoxifen, leading to tamoxifen-resistant breast cancer. Recent evidence has implicated HER2 signaling in resistance to the EGFR-targeted cancer drug cetuximab.

Furthermore, diverse structural alterations have been identified that cause ligand-independent firing of this receptor, doing so in the absence of receptor over-expression. As stated the HER2 is found in a variety of tumors and some of these tumors carry point mutations in the sequence specifying the transmembrane domain of HER2. The resulting substitution of a valine for a glutamic acid results in the constitutive dimerization of this protein in the absence of a ligand.

B. MUC1 and HER2

MUC1 interacts with members of the ErbB receptor family (Li et al., 2001b; Li et al., 2003c; Schroeder et al., 2001) and with the Wnt effector, β-catenin (Yamamoto et al., 1997). The epidermal growth factor receptor and c-Src phosphorylate the MUC1 cytoplasmic domain (MUC1-CD) on Y-46 and thereby increase binding of MUC1 and β-catenin (Li et al., 2001a; Li et al., 2001b). Binding of MUC1 and β-catenin is also regulated by glycogen synthase kinase 3β and protein kinase Cδ (Li et al., 1998; Ren et al., 2002). MUC1 colocalizes with β-catenin in the nucleus (Baldus et al., 2004; Li et al., 2003a; Li et al., 2003c; Wen et al., 2003) and coactivates transcription of Wnt target genes (Huang et al., 2003). Other studies have shown that MUC also binds directly to p53 and regulates transcription of p53 target genes (Wei et al., 2005). Notably, overexpression of MUC1 is sufficient to induce anchorage-independent growth and tumorigenicity (Huang et al., 2003; Li et al., 2003b: Ren et al., 2002; Schroeder et al., 2004).

III. MUC1 Peptides

A. Structure

The present invention contemplates the design, production and use of various MUC1 peptides. The structural features of these peptides are as follows. First, the peptides have no more than 20 consecutive residues of MUC1. Thus, the term "a peptide having no more than 20 consecutive residues," even when including the term "comprising," cannot be understood to comprise a greater number of consecutive MUC1 residues. Second, the peptides will contain the CQC motif, and may also include the CQCR motif, CQCRR motif and the CQCRRK motif. Thus, the peptides will have, at a minimum, these three consecutive residues of the MUC1-C domain. Third, the peptides will have at least one amino acid residue attached to the NH₂-terminal side of the first C residue in the CQC motif, such that the first C residue is "covered" by that at least one amino acid attached thereto. This residue may be native to MUC1 (i.e., from the transmembrane domain), may be selected at random (any of the 20 naturally-occurring amino acids or analogs thereof), or may be part of another peptide sequence (e.g., a tag sequence for purification, a stabilizing sequence, or a cell delivery domain).

In general, the peptides will be 50 residues or less, again, comprising no more than 20 consecutive residues of MUC1. The overall length may be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 residues. Ranges of peptide length of 4-50 residues, 5-50 residues, 6-50 residues, 7-50 residues, 7-25, residues, 4-20 residues, 5-20 residues, 6-20 residues, 7-20 residues, and 7-15 residues are contemplated. The number of consecutive MUC1 residues may be 4, 5, 6, 7, 8, 9, 10, 11, 12, 13, 14, 15, 16, 17, 18, 19 or 20. Ranges of consecutive residues of 4-20 residues, 5-20 residues, 6-20 residues, 7-20 residues and 4-15 residues, 5-15, residues, 6-15 residues or 7-15 residues are contemplated.

The present invention may utilize an L-configuration amino acids. D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally-occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

As mentioned above, the present invention contemplates fusing or conjugating a cell delivery domain (also called a cell delivery vector, or cell transduction domain). Such domains are well known in the art and are generally characterized as short amphipathic or cationic peptides and peptide derivatives, often containing multiple lysine and arginine resides (Fischer, 2007). Of particular interest are poly-D-Arg and poly-D-Lys sequences (e.g., dextrorotary residues, eight residues in length), while others are shown in Table 1, below.

TABLE 1

| CDD/CTD PEPTIDES | SEQ ID NO |
| --- | --- |
| QAATATRGRSAASRPTERPRAPARSASRPRRPVE | 5 |
| RQIKIWFQNRRMKWKK | 6 |
| RRMKWKK | 7 |

TABLE 1-continued

| CDD/CTD PEPTIDES | SEQ ID NO |
| --- | --- |
| RRWRRWWRRWWRRWRR | 8 |
| RGGRLSYSRRRFSTSTGR | 9 |
| YGRKKRRQRRR | 10 |
| RKKRRQRRR | 11 |
| YARAAARQARA | 12 |
| RRRRRRRR | 13 |
| KKKKKKKK | 14 |
| GWTLNSAGYLLGKINLKALAALAKXIL | 15 |
| LLILLRRRIRKQANHSK | 16 |
| SRRHHCRSKAKRSRHH | 17 |
| NRARRNRRRVR | 18 |
| RQLRIAGRRLRGRSR | 19 |
| KLIKGRTPIKFGK | 20 |
| RRIPNRRPRR | 21 |
| KLALKLALKALKAALKLA | 22 |
| KLAKLAKKLAKLAK | 23 |
| GALFLGFLGAAGSTNGAWSQPKKKRKV | 24 |
| KETWWETWWTEWSQPKKKRKV | 25 |
| GALFLGWLGAAGSTMGAKKKRKV | 26 |
| MGLGLHLLVLAAALQGAKSKRKV | 27 |
| AAVALLPAVLLALLAPAAANYKKPKL | 28 |
| MANLGYWLLALFVTMWTDVGLCKKRPKP | 29 |
| LGTYTQDFNKFHTFPQTAIGVGAP | 30 |
| DPKGDPKGVTVTVTVTVTGKGDPXPD | 31 |
| PPPPPPPPPPPPPPP | 32 |
| VRLPPPVRLPPPVRLPPP | 33 |
| PRPLPPPRPG | 34 |
| SVRKRPRPPYLPRPRPPPFFPPRLPPRIPP | 35 |
| TRSSRAGLQFPVGRVHRLLRK | 36 |
| GIGKFLHSAKKFGKAFVGEIMNS | 37 |
| KWKLFKKIEKVGQNIRDGIIKAGPAVAVVGQATQIAK | 38 |
| ALWMTLLKKVLKAAAKAALNAVLVGANA | 39 |
| GIGAVLKVLTTGLPALISWIKRKRQQ | 40 |
| INLKALAALAKKIL | 41 |
| GFFALIPKIISSPLPKTLLSAVGSALGGSGGQE | 42 |
| LAKWALKQGFAKLKS | 43 |
| SMAQDIISTIGDLVKWIIQTVNXFTKK | 44 |
| LLGDFFRKSKEKIGKEFKRIVQRIKQRIKDFLANLVPRTES | 45 |

TABLE 1-continued

| CDD/CTD PEPTIDES | SEQ ID NO |
|---|---|
| LKKLLKKLLKKLLKKLLKKL | 46 |
| KLKLKLKLKLKLKLKLKL | 47 |
| PAWRKAFRWAWRMLICKAA | 48 |

Also as mentioned above, peptides modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino- and/or carboxyl-terminal residues.

The molecules according to the present invention can be delivered by encapsulating or embedding in a delivery vehicle. For example, liposomes, which are artificially prepared vesicles made of lipid bilayers have been used to delivery a variety of drugs. Liposomes can be composed of naturally-derived phospholipids with mixed lipid chains (like egg phosphatidylethanolamine) or other surfactants. In particular, liposomes containing cationic or neutral lipids have been used in the formulation of drugs. Liposomes should not be confused with micelles and reverse micelles composed of monolayers, which also can be used for delivery.

Nanoparticles are generally considered to be particulate substances having a diameter of 100 nm or less. In contrast to liposomes, which are hollow, nanoparticles tend to be solid. Thus, the drug will be less entrapped and more either embedded in or coated on the nanoparticle. Nanoparticles can be made of metals including oxides, silica, polymers such as polymethyl methacrylate, and ceramics. Similarly, nanoshells are somewhat larger and encase the delivered substances with these same materials. Either nanoparticles or nanoshells permit sustained or controlled release of the peptide or mimetic, and can stabilize it to the effects of in vivo environment.

Another modification for delivery of polypeptides is PEG-ylation. PEG-ylation is the process of covalent attachment of polyethylene glycol polymer chains to another molecule, normally a drug or therapeutic protein. PEG-ylation is routinely achieved by incubation of a reactive derivative of PEG with the target macromolecule. The covalent attachment of PEG to a drug or therapeutic protein can "mask" the agent from the host's immune system (reduced immunogenicity and antigenicity), increase the hydrodynamic size (size in solution) of the agent which prolongs its circulatory time by reducing renal clearance. PEG-ylation can also provide water solubility to hydrophobic drugs and proteins. Exemplary PEG-ylation technologies are described in U.S. Pat. Nos. 7,666,400, 7,610,156, 7,587,286, 6,552,170 and 6,420,339.

B. Synthesis

It will be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the 20 standard amino acids can can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

C. Linkers

Linkers or cross-linking agents may be used to fuse MUC1 peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

Another use of linkers in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge the physically constrains the peptide into its native α-helical shape. In addition to helping retain the native structure needed to interact with a target molecule, this conformation also provides stability against peptidases as well as cell-permeating properties. U.S. Pat. Nos. 7,192,713 and 7,183,059, describing this technology, are hereby incorporated by reference. See also Schafmeister et al., *Journal of the American Chemical Society,* 2000, 122(24): p. 5891-5892.

D. Design, Variants and Analogs

The present invention focuses on peptides comprising the sequence CQC. Having identified this key structure in MUC1 oligomer formation, the inventors also contemplate that variants of the CQC sequence may be employed. For example, certain non-natural amino acids that satisfy the structural constraints of the CQC sequence may be substituted without a loss, and perhaps with an improvement in, biological function. In addition, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

Also of interest are peptidomimetic compounds that are designed based upon the amino acid sequences of compounds of the invention that are peptides. Peptidomimetic compounds are synthetic compounds having a three-dimensional conformation "motif" that is substantially the same as the three-dimensional conformation of a selected peptide. The peptide motif provides the peptidomimetic compound with the ability to inhibit the oligomerization of MUC1. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

IV. Therapies

A. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render materials stable and allow for uptake by target cells. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intraperitoneal, or intravenous injection. Such compositions would normally be administered as pharmaceutically acceptable compositions, described supra. Of particular interest is direct intratumoral administration, perfusion of a tumor, or admininstration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Cancer Types and Subjects

Cancer cells to which the methods of the present invention can be applied include generally any cell that expresses HER2, and more particularly, that overexpresses HER2. An appropriate cancer cell can be a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. In addition, the methods of the invention can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

C. Treatment Methods

Peptides or analogs that inhibit MUC1 oligomer formation are generally useful as anti-cancer therapeutics or prophylactics. They can be administered to mammalian subjects (e.g., MUC1+/HER2+ cancer patients) alone or in conjunction with other drugs and/or radiotherapy, in particular anti-HER2 therapies. The compounds can also be administered to subjects that are genetically and/or environmentally (due to, for example, physiological and/or environmental factors) susceptible to cancer, e.g., subjects with a family history of cancer (e.g., breast cancer), subjects with chronic inflammation or subject to chronic stress, or subjects that are exposed to natural or non-natural environmental carcinogenic conditions (e.g., excessive exposure to sunlight, industrial carcinogens, or tobacco smoke).

When the methods are applied to subjects with cancer, prior to administration of a compound, the cancer can optionally be tested for MUC1 expression (MUC protein or MUC mRNA expression) by methods known in the art. In this way, subjects can be identified as having a MUC1-expressing or overexpressing cancer. Such methods can be performed in vitro on cancer cells obtained from a subject. Alternatively, in vivo imaging techniques using, for example, radiolabeled antibodies specific for MUC1 can be performed. In addition, body fluids (e.g., blood or urine) from subjects with cancer can be tested for elevated levels of MUC1 protein or MUC1 protein fragments.

The dosage required depends on the choice of the route of administration: the nature of the formulation; the nature of the patient's illness; the subject's size, weight, surface area, age, and sex; other drugs being administered; and the judgment of the attending physician. Suitable dosages are in the range of 0.0001 mg/kg-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 5-, 6-, 8-, 10-, 20-, 50-, 100-, 150-, or more times). Encapsulation of the polypeptide in a suitable delivery vehicle (e.g., polymeric microparticles or implantable devices) may increase the efficiency of delivery, particularly for oral delivery.

D. Combination Therapies

As mentioned above, it is common for HER2+ cancers to be non-responsive to trastuzamab, or to become so within a year of receiving trastuzamab treatment. One general approach to such problems combine cancer therapies as a way of increasing their efficacy. While such approaches can be successful, it is entirely unclear whether any two therapies will work in concert to inhibit a given type of cancer. In the context of the present invention, the inventors have shown that MUC1 peptide therapy can be used successfully in conjunction with an anti-HER2 agent to render resistant cells sensitive to treatment.

To kill cells, inhibit cell growth, inhibit metastasis, inhibit angiogenesis or otherwise reverse or reduce the malignant phenotype of tumor cells, using the methods and compositions of the present invention, one would generally contact a target cell with a MUC1 peptide and an anti-HER2 therapy. These therapies would be provided in a combined amount effective to kill or inhibit proliferation of the cell. This process may involve contacting the cells with the agents/therapies at the same time. This may be achieved by contacting the cell with a single composition or pharmacological formulation that includes both therapies, or by contacting the cell with two distinct compositions or formulations, at the same time, wherein one composition includes the MUC1 peptide and the anti-HER2 therapy.

Alternatively, the MUC1 treatment may precede or follow the anti-HER2 therapy by intervals ranging from minutes to weeks. In embodiments where the anti-HER2 therapy and the MUC1 peptide are applied separately to the cell, one would generally ensure that a significant period of time did not expire between the time of each delivery, such that the therapies would still be able to exert an advantageously combined effect on the cell. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the MUC1 peptide or the anti-HER2 therapy will be desired. Various combinations may be employed, where the MUC1 peptide is "A" and the anti-HER2 therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated. Again, to achieve cell killing, both therapies are delivered to a cell in a combined amount effective to kill the cell. In addition to trastuzamab, lapatinib and pertuzumab are further anti-HER2 agents that may be used in combination with the present invention.

E. Additional Combinations

In conjunction with the aforementioned combination therapy, other agents or factors or therapies may be suitable for combined use. These include can include any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic" or "genotoxic agents," are intended to be of use in the combined treatment methods disclosed herein. In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition.

Various classes of chemotherapeutic agents are comtemplated for use with in combination with peptides of the present invention, for example, selective estrogen receptor antagonists ("SERMs"), such as Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene.

Chemotherapeutic agents contemplated to be of use include, e.g., camptothecin, actinomycin-D amd mitomycin C. The invention also encompasses the use of a combination of one or more DNA damaging agents, whether radiation-based or actual compounds, such as the use of X-rays with cisplatin or the use of cisplatin with etoposide. The agent may be prepared and used as a combined therapeutic composition, or kit, by combining it with a MUC1 peptide, as described above.

Heat shock protein 90 is a regulatory protein found in many eukaryotic cells. HSP90 inhibitors have been shown to be useful in the treatment of cancer. Such inhibitors include Geldanamycin, 17-(Allylamino)-17-demethoxygeldanamycin. PU-H71 and Rifabutin.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include Adriamycin, also known as Doxorubicin, Etoposide, Verapamil, Podophyllotoxin, and the like. Widely used in a clinical setting for the treatment of neoplasms, these compounds are administered through bolus injections intravenously at doses ranging from 25-75 mg/m$^2$ at 21 day intervals for Doxorubicin, to 35-50 mg/m$^2$ for etoposide intravenously or double the intravenous dose orally. Microtubule inhibitors, such as taxanes, also are contemplated. These molecules are diterpenes produced by the plants of the genus *Taxus*, and include paclitaxel and docetaxel.

Epidermal growth factor receptor inhibitors, such as Iressa, mTOR, the mammalian target of rapamycin, also known as FK506-binding protein 12-rapamycin associated protein 1 (FRAP1) is a serine/threonine protein kinase that regulates cell growth, cell proliferation, cell motility, cell survival, protein synthesis, and transcription. Rapamycin and analogs thereof ("rapalogs") are therefore contemplated for use in combination cancer therapy in accordance with the present invention.

Another possible combination therapy with the peptides claimed herein is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors affect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the local or regional delivery of MUC1 peptides to patients with cancer will be a very efficient method for treating the clinical disease. Similarly, the chemo- or radiotherapy may be directed to a particular, affected region of the subject's body. Alternatively, regional or systemic delivery of expression construct and/or the agent may be appropriate in certain circumstances, for example, where extensive metastasis has occurred.

In addition to combining MUC1 therapies with chemo- and radiotherapies, it also is contemplated that combination with immunotherapy, hormone therapy, toxin therapy and surgery.

It also should be pointed out that any of the foregoing therapies may prove useful by themselves in treating cancer.

V. EXAMPLES

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell culture. SKBR3 and BT474 cells were obtained from ATCC (Rockville, Md.). SKBR3 and BT474 were maintained in McCoy's 5a modified medium and Dulbecco's modified Eagle medium/Ham F12 (1:1) supplemented with 10% heat-inactivated FBS, 100 units/ml penicillin, 100 gi/ml streptomycin, and 2 mM L-glutamine. SKBR 3R and BT474R cells were selected for resistance to trastuzumab as described (32). Cells were treated with GO-203 and CP-2 peptides (AnaSpec). Trastuzumab (Genentech) was dissolved in sterile apyrogen water (stock solution of 21 mg/ml) and stored at 4° C. Viability was determined by trypan blue exclusion.

Immunoprecipitation and immunoblot analysis. Cell lysates were prepared as described (31). Soluble proteins were immunoprecipitated with anti-MUC1-C (Ab5; Neomarkers), anti-HER3 (Cell Signaling Technology) or a control IgG. The precipitates and lysates not subjected to immunoprecipitation were immunoblotted with anti-HER2 (Cell Signaling Technology), anti-MUC1-C, anti-β-actin (Sigma-Aldrich), anti-p-HER2 Tyr1221/1222, anti-HER2, anti-p-HER3 Tyr1289, anti-HER3, anti-p-AKT S473 and anti-AKT (Cell Signaling Technology). Reactivity was detected with horseradish peroxidase-conjugated secondary antibodies and chemiluminescence.

In vitro binding assay. GST and GST-MUC1-CD fusion proteins were prepared and incubated with cell lysates as described (26). Adsorbates to glutathione-conjugated beads were analyzed by immunoblotting.

Determination of $IC_{50}$ and synergism. Cells were seeded on 96-well plates in 100 μl of growth medium at a density of 3000 cells per well. After 24 h, the cells were exposed to drugs in treatment medium for an additional 72 h. Cell viability was assessed using the alamar blue viability assay (Invitrogen). Triplicate wells of each treatment were analyzed and each experiment was done three times. The $IC_{50}$ values were determined by nonlinear regression of the dose-response data using Prism 5.0 for Mac OSX (GraphPad Software). The presence or absence of synergism between GO-203 and trastuzumab was determined by the method of Chou and Talalay (33, 34). Briefly, cells were exposed to 1:1 ratios of the respective $IC_{50}$ values for GO-203 and trastuzumab at (i) ¼×$IC_{50}$, (ii) ½×$IC_{50}$, (iii) $IC_{50}$, (iv) 2×$IC_{50}$, and (v) 4×IC50. Cell viability was determined after treatment for 72 h. The combination index (CI) was calculated to determine the presence of synergism (CI<1) or antagonism (CI>1) using CalcuSyn software (Biosoft).

Colony formation assays. Cells were seeded onto six-well plates and incubated for 10-14 days. The cells were then washed and stained with 0.5% crystal violet in 25% methanol. Colonies 425 cells were counted in triplicate wells.

Trastuzumab-resistant BT474R tumor xenograft model. Four- to 6-week-old BALB/c nu/nu female mice were injected subcutaneously with 1×10[7] BT474R cells in the flank. When tumors were approx., 80-100 mm[3], the mice were pair-matched into control and treatment groups of eight mice each. Phosphate-buffered saline (control vehicle) or GO-203 at 7.5 mg/kg body weight was administered daily by intravenous injection for 21 days. Tumor volumes were calculated as described (Raina et al., 2011).

Assessment of drug interaction by Bliss independence. The BI model was also used to assess the interaction between GO-203 and trastuzumab in studies of trastuzumab-resistant cells. BI was determined using the equation $Ei = E_A + E_B - (E_A \times E_B)$ (Buck et al., 2006; Guertin et al., 2012), where EA is the fractional inhibition for GO-203 alone and EB is that for trastuzumab alone. Using this equation, if the experimentally measured inhibition is greater than Ei, then the combination is synergistic.38 Plots were generated by Prism GraphPad software.

Example 2

Results

Silencing MUC1-C suppresses HER2 activation. MUC1 associates with HER2 in non-HER2-amplified breast cancer cells and this interaction is increased by heregulin stimulation.23 However, the functional significance of the MUC1-C/HER2 interaction has remained unclear. Accordingly, studies were performed on SKBR3 and BT474 breast cancer cells that overexpress HER2 and are dependent on phosphorylated HER2 (p-HER2) for growth and survival.3 Levels of HER2 and MUC1-C were found to be similar in these cells (FIG. 1A). Coimmunoprecipitation studies further demonstrated that MUC1-C associates with HER2 in both SKBR3 and BT474 cells (FIG. 1B). To assess the potential effects of MUC1-C on HER2 signaling, the inventors stably silenced MUC1-C in SKBR3 cells (FIG. 1C, left). Notably, MUC1-C silencing was associated with the downregulation of p-HER2, but not HER2, abundance, consistent with a decrease in HER2 activation (FIG. 1C, left). In concert with these results, silencing MUC1-C in BT474 cells similarly resulted in suppression of p-HER2 levels (FIG. 1C, right). MUC1-C silencing was also associated with a decrease in SKBR3 cell growth (FIG. 1D, left) and BT474 cell growth (FIG. 1D, right). Moreover, colony formation was substantially decreased by silencing MUC1-C expression in both SKBR3 (FIG. 1E, left) and BT474 (FIG. 1E, right) cells. These findings indicated that MUC1-C contributes to HER2 activation and proliferation of HER2-overexpressing breast cancer cells.

The MUC1-C inhibitor, GO-203, downregulates HER2 phosphorylation. The 72-aa MUC1-CD contains a CQC motif that is necessary for its homodimerization (Leng et al., 2007 and Raina et al., 2012) (FIG. 2A). The results of pull-down studies using lysates from SKBR3 cells demonstrated that MUC1-CD is sufficient for forming complexes with HER2 (FIG. 2A, left). However, binding to HER2 was not detectable with MUC1-CD in which the CQC motif had been mutated to AQA (FIG. 2A, left). Similar results were obtained when pull-down experiments were indicating that the MUC1-C cysteine residues are of importance for forming MUC1-C/HER2 complexes. GO-203 is a cell-penetrating peptide that contains a poly-Arg cell transduction domain linked to CQCRRKN that binds to the MUC1-C-CD at the CQC motif and thereby blocks MUC1-C homodimerization (Raina et al., 2011, Riana et al., 2009 and Raina et al., 2012) (FIG. 2B). Another cell-penetrating peptide, designated CP-2, was synthesized in which the cysteine residues are altered to alanines, resulting in an inactive control that does not inhibit MUC1-C homodimerization (Raina et al., 2011, Riana et al. 2009 and Raina et al., 2012) (FIG. 2B). Treatment of SKBR3 cells with GO-203 disrupted the interaction between MUC1-C and HER2 (FIG. 2B, left). By contrast, CP-2 had no apparent effect on the abundance of MUC1-C/HER2 complexes (FIG. 2B, left). GO-203, but not CP-2, also blocked the interaction between MUC1-C and HER2 in BT474 cells (FIG. 2B, right). Analysis of p-HER2 levels further demonstrated that GO-203, but not CP-2, decreases HER2 activation in SKBR3 cells (FIG. 2C, left and right). BT474 cells also responded to GO-203, and not CP-2, exposure with decreased HER2 activation (FIG. 2D). In concert with these results, GO-203 treatment of SKBR3 (FIG. 2E) and BT474 (FIG. 2F) cells was associated with inhibition of growth. These findings and those obtained with MUC1-C silencing provided support for the premise that binding of MUC1-C and HER2 contributes to HER2 activation.

MUC1-C/HER2 complexes are upregulated in association with trastuzumab resistance. Trastuzumab-resistant SKBR3R cells were generated by chronic exposure to increasing concentrations of trastuzumab for over 18 months in vitro (Scaltriti et al., 2011). Thus, in contrast to parental SKBR3 cells, growth of the resistant SKBR3R cells was not inhibited by exposure to 80 nM trastuzumab (FIG. 3A). Levels of HER2 and MUC1-C were similar in SKBR3 and SKBR3R cells (FIG. 3B). Strikingly, however, MUC1-C/HER2 complexes were 19-fold higher (as determined by densitometric scanning of the signals) in the resistant SKBR3R cells (FIG. 3C). Analysis of trastuzumab-resistant BT474R cells (Scaltritl et al., 2011) (FIG. 3D) also demonstrated similar levels of MUC1-C and HER2 as compared with that in the sensitive BT474 cells (FIG. 3E). Moreover, BT474R cells exhibited a substantial increase (28-fold) in MUC1-C/HER2 complexes (FIG. 3F), indicating that the interaction between MUC1-C and HER2 is increased in the setting of trastuzumab resistance.

Targeting MUC1-C suppresses HER2 activation in trastuzumab-resistant cells. As found in wild-type SKBR3 cells, stable silencing of MUC1-C in SKBR3R (FIG. 4A) and BT474R (FIG. 4B) cells was associated with decreases in p-HER2 levels, indicating that MUC1-C also contributes to HER2 activation in trastuzumab-resistant cells. Densitometric scanning of the p-HER2 signals from multiple experiments demonstrated a decrease in p-HER2 abundance of 74% and 45% in the SKBR3R and BT474R cells, respectively (FIGS. 6A-B). In studies with SKBR3R cells, the inventors found that treatment with GO-203 is associated with disruption of MUC1-C/HER2 complexes (FIG. 4C). Similar results were obtained when BT474R cells were treated with the MUC1-C inhibitor (FIG. 4D). GO-203 also suppressed HER2 activation in both SKBR3R (FIG. 4E) and BT474R (FIG. 4F) cells. These results indicate that targeting MUC1-C with silencing or GO-203 treatment results in the suppression of HER2 activation in trastuzumab-resistant cells.

Targeting MUC1-C suppresses HER3 phosphorylation. HER2 phosphorylates HER3 and disruption of the HER2/HER3 interaction is associated with HER3 dephosphorylation (Junttila et al., 2009). These findings and the demonstration that targeting MUC1-C downregulates HER2 invoked the possibility that MUC1-C inhibition could also affect HER3 activation. Indeed, silencing MUC1-C in SKBR3R and BT474R cells was associated with decreases in p-HER3 levels (FIG. 5A, left and right). Scanning of the p-HER3 signals from multiple experiments demonstrated a decrease in p-HER3 abundance of 55% and 52% in the SKBR3R and BT474R cells, respectively (FIGS. 1C-D). HER3 is as crucial as HER2 in promoting proliferation of breast cancer cells that overexpress HER2 (Lee-Hoeflich et al., 2008). In that sense, the suppression of both phosphorylated HER2 (FIGS. 4A-B) and HER3 (FIG. 5A) was associated with a marked decrease in colony formation (FIG. 5B, left and right). GO-203 treatment of SKBR3R cells also suppressed p-HER3 abundance and activation of the downstream effector AKT (FIG. 5C). AKT phosphorylates the CDK inhibitor p27 on T198 and thereby inactivates p27 by preventing its localization to the nucleus (Viglietto et al., 2002 and Motti et al., 2004). In concert with the GO-203-induced decreases in AKT activation, phosphorylation of p27 was also decreased in the absence of apparent changes in p27 abundance (FIG. 5C). Trastuzumab resistance is associated with increases in p27 phosphorylation (Lee-Hoeflich et al., 2011) and upregulation of cyclin E (Scaltriti et al., 2011). In addition to the decreases in phospho-p27 levels, the inventors also found that GO-203 treatment is associated with the downregulation of cyclin E abundance (FIG. 5C). Moreover, GO-203 treatment of SKBR3R cells was associated with inhibition of growth (FIG. 5D). Similar effects of GO-203 treatment were obtained in BT474R cells with decreases in phospho-p27 and cyclin E levels (FIG. 5E) and an arrest of growth in vitro (FIG. 5F), and as tumor xenografts in nude mice (FIG. 5G). These findings thus indicate that silencing MUC1-C or inhibition of MUC1-C with GO-203 results in the downregulation of HER3 activation and suppression of cell growth and survival.

Targeting MUC1-C with silencing or GO-203 treatment reverses trastuzumab resistance. The demonstration that MUC1-C promotes HER2 signaling invoked the possibility that targeting MUC1-C might affect the response to trastuzumab. In this context, analysis of SKBR3R cells demonstrated that silencing MUC1-C is associated with increased sensitivity to the growth inhibitory effects of trastuzumab (FIG. 6A). Trastuzumab resistance of BT474R cells was also reversed in part by silencing MUC1-C (FIG. 6B), indicating that targeting MUC1-C might be effective in combination with trastuzumab. To assess the effects of combining GO-203 and trastuzumab, the inventors first identified the half-maximal inhibitory concentrations ($IC_{50}$s) for each agent against SKBR3 and BT474 cells. In studies with SKBR3 cells, the $IC_{50}$s for GO-203 and trastuzumab were 5.9 mM and 93 nM, respectively (Table 1A). Based on the Chou-Talalay method, the inventors then evaluated the effects of combining GO-203 and trastuzumab. As shown in the dose-effect curves, treatment of SKBR3 cells with the combination was more effective in inhibiting growth and survival than that obtained with either agent alone (FIG. 6C, left). The median-effect analysis and calculation of the median dose values further showed a B3-fold reduction in the median dose for GO-203 in the presence of trastuzumab as compared with GO-203 alone (FIG. 6C, right). Calculation of the combination index (CI) at the $ED_{50}$, $ED_{75}$ and $ED_{90}$ for these agents demonstrated a high degree of synergy with the values ol (Table 1B). Comparable results were obtained when BT474 cells were treated with GO-203 and trastuzumab as shown in the dose-effect curves (FIG. 8A, left) and the median-effect plots (FIG. 8A, right), and as supported by CI values ranging from 0.47 to 0.68 (Table 1B). $IC_{50}$s for GO-203 were also generated for the SKBR3R and BT474R cells (Table 1A). For these trastuzumab-resistant cells, there is no definable $IC_{50}$ for trastuzumab (Table 1A); accordingly, the inventors used the Bliss independence (BI) method for assessing interactions between two agents when one of the agents is inactive.[37,38] As expected, treatment with trastuzumab alone at 40 nM had no effect on SKBR3R cell growth. However, GO-203 alone was effective in inhibiting growth, and combining GO-203 with 40 nM trastuzumab was more effective than either agent alone (FIG. 6D, left and right), indicating that GO-203 reverses resistance to trastuzumab. An observed BI score of 0.84 as compared with 0.46 for the predicted BI supported a synergistic interaction (Table 2). Based on these findings, the inventors used the Chou-Talalay method to further analyze the interaction between GO-203 and trastuzumab. Under these experimental conditions, the inventors confirmed that the combination of GO-203 and trastuzumab is synergistic in the treatment of SKBR3R cells (FIG. 6E) with the CI<1 (Table 1B). GO-203 was also highly effective in combination with trastuzumab in the treatment of trastuzumab resistant BT474R cells using the BI (FIG. 8B and Table 2) and Chou-Talalay (FIG. 8C and Table 1B) methods. These findings indicate that GO-203 is synergistic with trastuzumab in the treatment of trastuzumab-resistant cells.

Effects of targeting MUC1-C on lapatinib treatment of trastuzumab-resistant cells. Lapatinib is a small-molecule ATP competitor that inhibits phosphorylation of the HER2 intracellular kinase domain and has reported activity in trastuzumab-resistant cells (Scaltriti et al. 2009, Wood et al. 2004, Konecny et al., 2006 and Nahta et al., 2007). In the present studies with SKBR3R cells, the combination of lapatinib and GO-203 was more effective in inhibiting growth than lapatinib alone (FIG. 9A, left and right). Synergy between lapatinib and GO-203 was supported by an observed BI score of 0.85 as compared with 0.58 for the predicted BI (Table 3). In addition, lapatinib was synergistically active with GO-203 in inhibiting growth of BT474R cells (FIG. 9B (left and right) and Table 3). Based on these observations, the inventors assessed the effects of (i) lapatinib alone, (ii) lapatinib+trastuzumab and (iii) lapatinib+trastuzumab+GO-203. Using SKBR3R cells, the lapatinib+trastuzumab combination was not significantly different in inhibiting growth as compared with lapatinib alone (FIG. 10A, left and right). However, the triple lapatinib+trastuzumab þ GO-203 combination was significantly more effective than lapatinib alone or lapatinib+trastuzumab (FIG. 10A, left and right) and as evidenced by an observed BI of 0.81 compared with a predicted BI of 0.59 (Table 4). These findings with the lapatinib+trastuzumab+GO-203 combination were further supported in studies of BT474R cells (FIG. 10B, left and right); Table 4), indicating that GO-203 potentiates the effects of both lapatinib and trastuzumab in trastuzumab-resistant cells.

Example 3

Discussion

MUC1-C is a previously unrecognized effector of HER2 activation. Previous work demonstrated that MUC1 associates with HER2 in the mammary glands of an MUC1 transgenic mouse model and in human non-HER2-amplified breast cancer cell lines (Kufe, 2013). To define the functional significance of this association, the present studies were performed on SKBR3 and BT474 breast cancer cells that overexpress HER2 and are dependent on HER2 for proliferation.

As anticipated, the inventors found that MUC1-C associates with HER2 in these HER2-overexpressing cells. Surprisingly, however, the inventors' results showed that silencing MUC1-C is associated with the downregulation of HER2 activation and loss of clonogenic survival, supporting the contention that MUC1-C is of importance to HER2 signaling. The MUC1-C subunit includes a CD that contains a CQC motif, which is necessary for the formation of MUC1-C homodimers (Leng et al., 2007). The inventors' results show that the MUC1-C CD is sufficient to form complexes with HER2 and that this association is abrogated by altering the CQC motif to AQA, indicating that MUC1-C homodimerization is necessary for the MUC1-C/HER2 interaction. Cell membrane-penetrating peptides, such as GO-203, block homodimerization of endogenous MUC1-C through binding to the CQC motif (Raina et al., 2009 and Raina et al. 2012). The present results demonstrating that treatment of HER2-overexpressing breast cancer cells with GO-203 blocks the interaction between MUC1-C and HER2 provided further support for the premise that MUC1-C homodimerization is necessary for forming complexes with HER2. In addition and as found with MUC1-C silencing, targeting MUC1-C with GO-203 treatment was associated with marked decreases in HER2 phosphorylation. Overexpression of HER2 in human breast cancer cells facilitates the formation of HER2/HER3 heterodimers, activation of HER2 and HER2-mediated phosphorylation of HER3 (Baselga and Swain, 2009). The importance of HER3 in the HER2/HER3 heterodimer is supported by the demonstration that loss of HER3 function attenuates HER2-mediated transformation (Holbro et al., 2003). In addition to the downregulation of HER2, the inventors found that targeting MUC1-C is associated with suppression of HER3 activation. These findings support a previously unrecognized model in which MUC1-C homodimerization contributes to HER2 activation and HER3 phosphorylation.

Patients with HER2-overexpressing breast cancers frequently display primary unresponsiveness or develop acquired resistance to trastuzumab therapy. Trastuzumab resistance has been attributed to the number of mechanisms, including activation of the phosphatidylinositol-3 kinase and SRC pathways (Nagata et al., 2004 and Berns et al., 2007). Selection for growth of BT474 cells in the presence of trastuzumab for 8 weeks has been associated with the upregulation of MUC1 expression (Fessler et al., 2009). However, the present results show that the development of trastuzumab resistance over 18 months has little if any effect on MUC1-C abundance in SKBR3R and BT474R cells. The basis for this discrepancy in the findings is not clear. Nonetheless, the present results demonstrate that trastuzumab resistance is associated with a substantial (approx. 20-fold) increase in the association of MUC1-C and HER2. Trastuzumab disrupts ligand-independent HER2/HER3 interactions in HER2-overexpressing cells (Junttila et al., 2009). The inventors' results indicate that targeting MUC1-C attenuates HER2 activation in trastuzumab-resistant cells. These findings raised the possibility that MUC1-C may contribute to trastuzumab resistance by promoting HER2-mediated signaling. Indeed, targeting MUC1-C was associated with downregulation of (i) p-HER3 and p-AKT levels, and (ii) phosphorylation of p27, an AKT substrate. In addition, targeting MUC1-C resulted in decreases in cyclin E abundance, a finding consistent with the demonstration that cyclin E levels decrease upon HER2 inhibition (Mittendorf et al., 2010). The downregulation of p27 phosphorylation could also be linked to decreases in cyclin E expression as a result of increased localization of p27 to the nucleus and thereby inhibition of CDK2, which in turn results in cyclin E degradation (Viglietto et al., 2002, Motti et al., 2004 and Li et al., 2004). Further studies will be needed to address the mechanistic basis for cyclin E downregulation in GO-203-treated trastuzumab-resistant cells. Nonetheless, as both phospho-p27 and cyclin E have been linked to trastuzumab resistance (Scaltriti et al., 2011, Nahta et al., 2004 and Lee-Hoeflich et al., 2011), the inventors treated trastuzumab-resistant cells with GO-203 in combination with trastuzumab. The observation that GO-203 and trastuzumab are highly synergistic lends further support to the premise that MUC1-C contributes to the trastuzumab-resistant phenotype by promoting HER2/HER3-AKT activation. These findings thus indicate that targeting MUC1-C can reverse trastuzumab resistance. In addition, the inventors' results indicate that GO-203 can potentiate the effects of lapatinib and the lapatinab þ trastuzumab combination in the SKBR3R and BT474R models. Translation of these findings with regard to the potential effectiveness of combining GO-203 with trastuzumab and/or lapatinib in the clinic will therefore require further study. In this respect, a Phase I trial of GO-203 is presently being completed for patients with refractory solid tumors and, based on the present results, this agent may be effective in combination with HER2 inhibitors in the setting of trastuzumab-resistant breast cancer.

Epithelia are single cell layers with apical-basal polarity that separate metazoans from the external environment. As such, robust defense mechanisms emerged during evolution to protect epithelial integrity. The mucins contribute in part to that defense by forming a protective physical barrier. The MUC1-N subunit is shed from the epithelial cell surface into this barrier as a first line of defense. In turn, the transmembrane MUC1-C subunit functions in a subsequent line of defense by signaling stress to the interior of the epithelial cell to promote repair, growth and survival. Importantly in this regard, the response of epithelial cells to stress is associated with loss of apical-basal polarity and activation of an HER2-mediated proliferation and survival program. With loss of polarity, the apical MUC1-C protein is transiently repositioned over the cell membrane, allowing it to interact with HER2, which is normally sequestered at the basolateral membrane (Kufe, 2013 and Kufe, 2009). The present results provide evidence that, in associating with HER2, MUC1-C contributes to HER2 activation and HER3 phosphorylation. Thus, a potential advantage of this interaction with MUC1-C could conceivably be prolonged HER2/HER3 signaling in the absence of ligand. The epithelial stress response is reversible such that the interaction between MUC1-C and HER2 is transient with return of epithelial cell polarity. By contrast, in carcinoma cells with sustained activation of the epithelial-mesenchymal transition, MUC1-C is positioned to constitutively interact with the HER2 complex and promote activation of the HER2 pathway. In this way, breast cancer cells would appear to have appropriated and subverted a physiologic stress response to support their own growth and survival. Importantly, the interaction between MUC1-C and HER2 has been increased further and subverted to circumvent the growth inhibitory effects of trastuzumab treatment, such that targeting MUC1-C reverses trastuzumab resistance.

TABLE 1A $IC_{50}$ Values of GO-203 and Trastuzumab

| Cell Lines | GO-203 (µM) | Trasutuzumab (nM) |
|---|---|---|
| SKBR3 | 5.9 | 93 |
| SKBR3R | 5.5 | ✗ |
| BT474 | 10.2 | 133 |
| BT474R | 9.5 | ✗ |

✗ Not definable

TABLE 1B

Combination Indices for GO-203 and Trastuzumab

| Cell Lines | ED50 | ED75 | ED90 |
|---|---|---|---|
| SKBR3 | 0.32 | 0.42 | 0.56 |
| SKBR3R | 0.47 | 0.56 | 0.68 |
| BT474 | 0.37 | 0.55 | 0.82 |
| BT474R | 0.55 | 0.72 | 0.94 |

TABLE 2

Bliss Independence Analysis for GO-203 and Trastuzumab

| Cell Lines | GO-203 (µM) $IC_{50}$ | GO-203 (µM) $IC_{50}$ with Trasutuzumab | Fold change | BI (predicted) | BI (observed) |
|---|---|---|---|---|---|
| SKBR3R | 6.2 | 4.0 | 1.55 | 0.46 | 0.84 |
| BT474R | 6.7 | 4.7 | 1.42 | 0.22 | 0.68 |

TABLE 3

Bliss Independence Analysis of Lapatinib and GO-203

| Cell Lines | Lapatinib (µM) $IC_{50}$ | Lapatinib (µM) $IC_{50}$ with GO-203 | Fold change | BI (predicted) | BI (observed) |
|---|---|---|---|---|---|
| SKBR3R | 1.36 | 0.94 | 1.45 | 0.58 | 0.85 |
| BT474R | 1.43 | 0.67 | 2.13 | 0.42 | 0.70 |

TABLE 4

Bliss Independence Analysis for Lapatinib Combined with Trastuzumab and GO-203

| Cell Lines | Lapatinib (µM) $IC_{50}$ | Lapatinib (µM) $IC_{50}$ with Trastuzumab | Lapatinib (µM) $IC_{50}$ with Trastuzumab and GO-203 | Fold Change | BI (predicted) | BI (observed) |
|---|---|---|---|---|---|---|
| SKBR3R | 1.7 | 1.5 | 0.93 | 1.82 | 0.59 | 0.81 |
| BT474R | 1.5 | 1.2 | 0.22 | 6.8 | 0.48 | 0.86 |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. REFERENCES

The following references, to the extent that they provide exemplary procedural or other details supplementary to those set forth herein, are specifically incorporated herein by reference:

U.S. Pat. No. 5,440,013
U.S. Pat. No. 5,446,128
U.S. Pat. No. 5,475,085
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,840,833
U.S. Pat. No. 5,859,184
U.S. Pat. No. 5,889,155
U.S. Pat. No. 5,929,237
U.S. Pat. No. 6,261,569
Abe and Kufe, Cancer Res., 49(11):2834-2839, 1989.
Baldus et al., Clin. Cancer Res., 10(8):2790-2796, 2004.
Baselga and Swain, Nat Rev Cancer, 9:463-475, 2009.
Berns et al., Cancer Cell, 12:395-402, 2007.
Bodanszky et al., J. Antibiot., 29(5):549-53, 1976.
Buck et al., Mol Cancer Ther, 5: 2676-2684, 2006.
Duraisamy et al., J Oncology, 31:671-7, 2007.
Fessler et al., Breast Cancer Res Treat. 118: 113-124, 2009.
Fischer, Med. Res. Rev., 27(6):755-796, 2007.
Gendler et al., J. Biol. Chem., 263:12820-12823, 1988.
Guertin et al., Cancer Cell Int, 12: 45, 2012.
Hodel et al., Mol. Cell, 10(2):347-58, 2002.
Holbro et al., Proc Natl Acad Sci USA, 100:8933-8, 2003.
Huang et al., Cancer Biol Ther., 2:702-706, 2003.
Huang et al., Cancer Res., 65:10413-10422, 2005.
Huang et al., Cancer Res. 70:1204-14, 2010.
Hynes et al., Nat Rev Cancer, 5:341-54, 2005.

Johnson et al., In: *Biotechnology And Pharmacy*, Pezzuto et al. (Eds.), Chapman and Hall, N Y, 1993.
Junttila et al., *Cancer Cell*, 15:429-40, 2009.
Kau et al., *Nat. Rev. Cancer,* 4(2):106-17, 2004.
Kinlough et al., *J. Biol. Chem.,* 279(51):53071-53077, 2004.
Klapper et al., *Cancer Res,* 60:3384-8, 2000.
Konecny et al., *Cancer Res.* 66:1630-1639, 2006.
Kufe et al., *Hybridoma.* 3:223-232, 1984.
Kufe, *Nature Reviews Cancer.* 9:874-85, 2009.
Kufe, *Oncogene,* 32:1073-81, 2013.
Lee-Hoeflich et al., *Cancer Res.* 68:5878-5887, 2008.
Lee-Hoeflich et al., *Cancer Discov,* 1:326-37, 2011.
Levitan et al., *J. Biol. Chem.,* 280:33374-33386, 2005.
Leng et al., *J Biol Chem,* 282:19321-30, 2007.
Li et al., *Mol. Cell Biol.,* 18:7216-7224, 1998.
Li et al., *J. Biol. Chem.,* 276:6061-6064, 2001.
Li et al., *J. Biol. Chem.,* 276:35239-35242, 2001.
Li et al., *Mol Cancer Res,* 1:765-75, 2003.
Li et al., *Oncogene,* 22:6107-6110, 2003a.
Li et al., *Cancer Biol. Ther.,* 2:187-193, 2003b.
Li et al., *Mol. Cancer Res.,* 1:765-775, 2003c.
Li et al., *J. Biol. Chem.,* 279:25260-25267, 2004.
Ligtenberg et al., *J. Biol. Chem.,* 267, 6171-6177, 1992.
Macao, *Nat. Struct. Mol. Biol.,* 13, 71-76, 2006.
Merlo et al., *Cancer Res.,* 49, 6966-6971, 1989.
Merrifield, *J. Am. Chem. Soc.,* 85:2149-2154, 1963.
Mittendorf et al., *Clin Cancer Res.* 15:7381-8, 2009.
Mittendorf et al., *Oncogene,* 29:3896-3907, 2010.
Motti et al., *Cell Cycle,* 3:1074-1080, 2004.
Nagata et al., *Cancer Cell.* 6:117-27, 2004.
Nahta et al., *Cancer Res.* 64:3981-6, 2004.
Nahta et al, *Cancer Res,* 65:11118-28, 2005.
Nahta et al, *Mol Cancer Ther.* 6:667-674, 207.
Peptide Synthesis, 1985
Percipalle et al., *J. Mol. Biol.,* (4):722-32, 1997.
Percy et al., *Cancer Res.,* 52(22):6365-6370, 1992.
Protective Groups in Organic Chemistry, 1973
Raina et al., *J Biol Chem.* 279:20607-12, 2004.
Raina et al., *J. Biol. Chem.,* 279:20607-20612, 2004.
Raina et al., *EMBO J.,* 25:3774-3783, 2006.
Raina et al., *Cancer Res,* 69:5133-41, 2009.
Raina et al., *Mol Cancer Therapeutics,* 10:806-16, 2011.
Raina et al., *Int J Oncol,* 40: 1643-1649, 2012
Remington's Pharmaceutical Sciences, 15$^{th}$ Ed., 1035-1038 and 1570-1580, 1990.
Remington's Pharmaceutical Sciences, 15$^{th}$ Ed., 3:624-652, 1990.
Ren et al. *Cancer Cell,* 5:163-175, 2004.
Ren et al., *J. Biol. Chem.,* 277:17616-17622, 2002.
Romond et al., *N Engl J Med.* 353:1673-84, 2005.
Ryan and Wente, *Curr. Opin. Cell Biol.,* 12(3):361-71, 2000.
Scaltriti et al. *J Natl Cancer Inst.* 99:628-38, 2007.
Scaltriti et al., *Oncogene,* 28:803-14, 2009.
Scaltriti et al., *Proc Natl Acad Sci USA.* 108:3761-6, 2011.
Schroeder et al., *J. Biol. Chem.,* 276(16):13057-13064 2001.
Schroeder et al., *Oncogene,* 23:5739-5747, 2004.
Shattuck et al., *Cancer Res.* 68:1471-7, 2008.
Shin et al., *Nat Med.* 8:1145-52, 2002.
Siddiqui et al., *Proc. Natl. Acad. Sci. USA,* 85:2320-2323, 1988.
Slamon et al., *Science.* 235:177-82, 1987.
Slamon et al., *N Engl J Med.* 344:783-92, 2001.
Solid Phase Peptide Synthelia, 1984
Spector and Blackwell, *J Clin Oncol.* 27:5838-47, 2009.
Suh and Gumbiner, *Exp. Cell Res.,* 290(2):447-56, 2003.
Vermeer et al., *Nature.* 422(6929):322-6, 2003.
Viglietto et al., *Nat. Med* 8:1136-1144, 2002.
Wei et al., *Cancer Cell,* 7:167-178, 2005.
Weis, Cell, 112(4):441-51, 2003.
Wen et al., *J. Biol. Chem.,* 278:38029-38039, 2003.
Wood et al., *Cancer Res.* 64:6652-6659, 2004.
Yamamoto et al., *J. Biol. Chem.,* 272:12492-12494, 1997.
Yin et al. *J. Biol. Chem.,* 279:45721-45727, 2004.
Yin et al. *J. Biol. Chem.,* 282:257-266, 2007.
Young et al., *Cell.* 112(1):41-50, 2003.
Zhang et al., *Nat Med* 17:461-9, 2011.

The invention claimed is:

1. A method of treating a human subject having mucin 1, cell surface associated (MUC1)-positive/human epidermal growth factor receptor 2-positive (HER2)-positive cancer comprising administering to said subject:
(a) a MUC1 peptide of at least 4 consecutive MUC1 residues and no more than 20 consecutive MUC1 residues and comprising the sequence CQC (SEQ ID NO:4), wherein the amino-terminal cysteine of CQC is covered on its $NH_2$-terminus by at least one amino acid residue that need not correspond to the native MUC-1 transmembrane sequence; and
(b) an anti-HER2 therapy,
wherein the cancer overexpresses HER2 as compared to a similar non-cancerous cell.

2. The method of claim 1, wherein said anti-HER2 therapy is trastuzumab, pertuzumab or lapatinib.

3. The method of claim 1, wherein said MUC1 peptide and/or said anti-HER2 therapy is administered to said subject more than once.

4. The method of claim 1, wherein said subject has previously received an anti-HER2 therapy.

5. The method of claim 1, wherein said subject has not previously received an anti-HER2 therapy.

6. The method of claim 1, wherein said cancer is recurrent and/or metastatic.

7. The method of claim 1, wherein the cancer is a carcinoma.

8. The method of claim 7, wherein the carcinoma is a gastric, prostate or breast carcinoma.

9. The method of claim 1, wherein said anti-HER2 therapy is administered prior to said peptide.

10. The method of claim 1, wherein said anti-HER2 therapy is administered after said peptide.

11. The method of claim 1, wherein said anti-HER2 therapy is administered at the same time as said peptide.

12. The method of claim 1, further comprising the step of assessing the expression of MUC1 in a tumor cell of said subject prior to administering said peptide.

13. The method of claim 1, further comprising the step of assessing the expression of HER2 in a tumor cell of said subject prior to administering said peptide.

14. The method of claim 1, wherein said method improves the response rate to said anti-HER2 therapy as compared to the anti-HER2 therapy given alone, or reverses resistance to said anti-HER2 therapy.

15. A method of treating a human subject having mucin 1, cell surface associated (MUC1)-positive/human epidermal growth factor receptor 2 (HER2)-positive cancer comprising administering to said subject:
(a) a MUC1 peptide of at least 4 consecutive MUC1 residues and no more than 20 consecutive MUC1 residues and comprising the sequence CQC (SEQ ID NO:4), wherein the amino-terminal cysteine of CQC is covered on its NH2-terminus by at least one amino acid residue that need not correspond to the native MUC-1 transmembrane sequence; and
(b) an anti-HER2 therapy,
wherein the subject has previous received an anti-HER2 therapy.

16. The method of claim 15, wherein said anti-HER2 therapy is trastuzumab, pertuzumab or lapatinib.

17. The method of claim 15, wherein said MUC1 peptide and/or said anti-HER2 therapy is administered to said subject more than once.

18. The method of claim 15, wherein said cancer is recurrent and/or metastatic.

19. The method of claim 15, wherein HER2 is overexpressed as compared to a similar non-cancerous cell.

20. The method of claim 15, wherein the cancer is a carcinoma.

21. The method of claim 20, wherein the carcinoma is a gastric, prostate or breast carcinoma.

22. The method of claim 15, wherein said anti-HER2 therapy is administered prior to said peptide.

23. The method of claim 15, wherein said anti-HER2 therapy is administered after said peptide.

24. The method of claim 15, wherein said anti-HER2 therapy is administered at the same time as said peptide.

25. The method of claim 15, further comprising the step of assessing the expression of MUC1 in a tumor cell of said subject prior to administering said peptide.

26. The method of claim 15, further comprising the step of assessing the expression of HER2 in a tumor cell of said subject prior to administering said peptide.

27. The method of claim 15, wherein said method improves the response rate to said anti-HER2 therapy as compared to the anti-HER2 therapy given alone, or reverses resistance to said anti-HER2 therapy.

28. A method of treating a human subject having mucin 1, cell surface associated (MUC1)-positive/human epidermal growth factor receptor 2 (HER2)-positive cancer comprising:
(a) assessing the expression of HER2 in a tumor cell of said subject;
(b) administering a MUC1 peptide of at least 4 consecutive MUC1 residues and no more than 20 consecutive MUC1 residues and comprising the sequence CQC (SEQ ID NO:4), wherein the amino-terminal cysteine of CQC is covered on its $NH_2$-terminus by at least one amino acid residue that need not correspond to the native MUC-1 transmembrane sequence; and
(c) administering an anti-HER2 therapy.

29. The method of claim 28, wherein said anti-HER2 therapy is trastuzumab, pertuzumab lapatinab.

30. The method of claim 28, wherein said MUC1 peptide and/or said anti-HER2 therapy is administered to said subject more than once.

31. The method of claim 28, wherein said subject has previously received an anti-HER2 therapy.

32. The method of claim 28, wherein said subject has not previously received an anti-HER2 therapy.

33. The method of claim 28, wherein said cancer is recurrent and/or metastatic.

34. The method of claim 28, wherein HER2 is overexpressed as compared to a similar non-cancerous cell.

35. The method of claim 28, wherein the cancer is a carcinoma.

36. The method of claim 35, wherein the carcinoma is a gastric, prostate or breast carcinoma.

37. The method of claim 28, wherein said anti-HER2 therapy is administered prior to said peptide.

38. The method of claim 28, wherein said anti-HER2 therapy is administered after said peptide.

39. The method of claim 28, wherein said anti-HER2 therapy is administered at the same time as said peptide.

40. The method of claim 28, further comprising the step of assessing the expression of MUC1 in a tumor cell of sad subject prior to administering said peptide.

41. The method of claim 28, wherein said method improves the response rate to said anti-HER2 therapy as compared to the anti-HER2 therapy given alone, or reverses resistance to said anti-HER2 therapy.

* * * * *

UNITED STATES PATENT AND TRADEMARK OFFICE
CERTIFICATE OF CORRECTION

PATENT NO. : 9,789,156 B2  
APPLICATION NO. : 14/774155  
DATED : October 17, 2017  
INVENTOR(S) : Donald W. Kufe et al.

Page 1 of 1

It is certified that error appears in the above-identified patent and that said Letters Patent is hereby corrected as shown below:

On the Title Page

Item (54), Line 5, and in the Specification, Column 1, delete "HEMOTHERAPEUTICS" and replace with --CHEMOTHERAPEUTICS-- therefor.

In the Claims

In Claim 1, Column 51, Line 16, delete the first occurrence of "-positive".

In Claim 15, Column 52, Line 13, delete "NH2-terminus" and insert --$NH_2$-terminus-- therefor.

In Claim 28, Column 52, Line 51, delete "receptor 2" and insert --receptor 2-- therefor.

In Claim 40, Column 53, Line 20, delete "sad" and insert --said-- therefor.

Signed and Sealed this  
Nineteenth Day of December, 2017

Joseph Matal  
*Performing the Functions and Duties of the*  
*Under Secretary of Commerce for Intellectual Property and*  
*Director of the United States Patent and Trademark Office*